United States Patent
Shukla

(10) Patent No.: US 9,360,427 B2
(45) Date of Patent: Jun. 7, 2016

(54) FLUORESCENT DETECTION OF CURING DIFFERENCE BETWEEN SURFACES

(71) Applicant: Deepak Shukla, Webster, NY (US)

(72) Inventor: Deepak Shukla, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 58 days.

(21) Appl. No.: 14/526,930

(22) Filed: Oct. 29, 2014

(65) Prior Publication Data

US 2016/0123881 A1 May 5, 2016

(51) Int. Cl.
*B29C 35/02* (2006.01)
*G01N 21/64* (2006.01)

(52) U.S. Cl.
CPC ........ *G01N 21/643* (2013.01); *G01N 2201/062* (2013.01)

(58) Field of Classification Search
CPC .... B29C 35/0288; C08J 3/248; G01N 21/643
See application file for complete search history.

(56) References Cited

U.S. PATENT DOCUMENTS

| | | |
|---|---|---|
| 3,091,651 A | 5/1963 | Soderquist et al. |
| 3,091,652 A | 5/1963 | Soderquist et al. |
| 4,651,011 A | 3/1987 | Ors et al. |
| 5,047,444 A | 9/1991 | DeVoe et al. |
| 5,633,313 A | 5/1997 | Blanchard et al. |

OTHER PUBLICATIONS

F. W. Wang et al., "Novel excimer fluorescence method for monitoring polymerization: 1. Polymerization of methyl methacrylate," *Polymer* (1984), 25, 690.
Ramin Vatanparast et al., "Monitoring of Curing of Polyurethane Polymers with Fluorescence Method," *Macromolecules* (2000), 33, 438-443.
Paula Bosch et al., "Fluorescent Probes for Sensins Processes in Polymers," *Chem. Eur. J.* (2005) 11, 4314-4325.
Dormond et al., "Uranium-Mediated Methylenation of Carbonyl Compounds," *J. Org. Chem.* (1987), 52, 688.
H. Stegemeyer, "Luminescence of Sterically Hindered Arylethylenes," *Phys. Chem.* (1968), 72, 335-340.
Dong et al., "The Py Scale of Solvent Polarities," *Can. J. Chem*, (1984), 62, 2560.

*Primary Examiner* — Elena T Lightfoot
(74) *Attorney, Agent, or Firm* — J. Lanny Tucker

(57) ABSTRACT

Pyrene can be used as a fluorescent probe for various industrial purposes. For example, it can be included in photocurable or thermally curable compositions and monitoring the fluorescence emission spectra before and after some curing will provide an indication of how much curing has occurred. Such monitoring can be carried out multiple times during a manufacturing process. Monitoring can also be done at different locations of a composition such as at inner and outer surfaces of a photocured or thermally cured layer.

13 Claims, 2 Drawing Sheets

FLUORESCENT DETECTION OF CURING DIFFERENCE BETWEEN SURFACES

RELATED APPLICATIONS

Reference is made to the following copending and commonly assigned patent applications, the disclosures of which are incorporated herein by reference:

U.S. Ser. No. 14/174,879 filed Feb. 7, 2014 by Shukla and Mis;

U.S. Ser. No. 14/197,293 filed Mar. 5, 2014 by Shukla and Mis; and

U.S. Ser. No. 14/526,909 filed on Oct. 29, 2014 by Shukla and entitled "Method for Fluorescent Detection of Curing".

FIELD OF THE INVENTION

This invention relates to a method for non-destructive monitoring of the extent of photocuring or thermal curing in various photocurable or thermally curable compositions, particularly photocurable compositions comprising acid-catalyzed compositions. This monitoring is carried out using pyrene as a fluorescent probe and measuring changes in a ratio of at least two peaks in fluorescence spectra measured at different times or in different environments. The method can be particularly suitable for on-line manufacturing processes wherein curing is carried out on one or both supporting sides of a transparent substrate.

BACKGROUND OF THE INVENTION

Composite polymer structures and coatings can be produced in a broad range of commercial processes. Often, such a composite or coating is formed using a polymerization reaction in which polymerizable reactants are mixed together and then cured, for example, by the addition of catalyst, heat, light, or a combination thereof. Accurate and complete curing is extremely important as the structure and properties of cured polymers strongly depend upon the extent of cure, both in amount and rate. Adhesion, abrasion, solvent resistance, and usefulness are usually diminished when a composite or coating is incompletely cured. Obviously, there is a desire to improve the curing of such compositions and even to know the extent of photocuring, for example, by a suitable monitoring procedure.

One technology in which photocuring monitoring is very important is in the fabrication of micro-electro mechanical devices (MEMS) that are becoming increasingly prevalent as low-cost, compact devices having a wide range of uses. For example, such devices can be included in for example, pressure sensors, accelerometers, gyroscopes, microphones, digital mirror displays, microfluidic devices, biosensors, and chemical sensors that would be apparent to one skilled in the art.

Cationically (acid catalyzed) photocured epoxy compositions and photoresists are commonly used to fabricate high resolution and high aspect ratio MEMS structures. Typically, such processes include depositing a layer of a photocurable epoxy photoresist composition onto a substrate. A mask is placed over the photocurable epoxy photoresist composition, which mask corresponds to a desired image or pattern. The mask blocks photocuring ultraviolet (UV) rays or other radiation in desired locations so that the photocurable epoxy photoresist composition is only selectively exposed and cured. With this type of photocurable epoxy photoresist composition, the exposing UV light will cause crosslinking or curing. Once the mask is in place, the photocurable epoxy photoresist composition was irradiated with the ultraviolet light. The portions of the photocurable epoxy photoresist composition that are not exposed will not be crosslinked or cured and are usually dissolved and removed by a suitable solvent after the exposure process, leaving the desired photocured pattern on the substrate. Verifying the extent of photocuring can be critical in determining highly effective process parameters for the fabrication of MEMS structures and devices.

Another area where the monitoring of photocuring is particularly important is with various photocurable coatings that are applied to continuous or web substrates. When a roll of continuous substrate in the form of a web is used, it should be thoroughly and evenly coated with a photocurable polymer. The substrate web is generally withdrawn from the roll and coated with a photocurable composition of appropriate reactants and photoinitiators as necessary for promoting a particular polymerization reaction. The coated web is then irradiated using a suitable light source to cause photocuring. The resulting photocured composition can be further processed in-line or rolled up for later use or further processing.

Known processes of measuring the extent of photocuring in these continuous webs generally utilize off-line methods, including non-destructive methods such as infrared or UV-visible absorption spectroscopy, and destructive methods such as solvent extraction, thermal analysis (glass transition temperature), and surface tack (for example as described in ASTM-D1640-83). All of these methods have inherent disadvantages.

A non-destructive, in-line method for monitoring the degree of photocuring is described in U.S. Pat. No. 4,651,011 (Ors et al.) in which a fluorescent material such as a dye is dissolved in a monomer, oligomer, or polymer and used to monitor the degree of curing or polymerization via fluorescence anisotropy or polarization by means of an optical inspection system.

Another method of monitoring the degree of photocuring utilizes fluorescence spectroscopy and probe molecules as described for example, by (a) F. W. Wang, R. E. Lowry, W. H. Grant, *Polymer* (1984), 25, 690; (b) Ramin Vatanparast, Shuyan Li, Kati Hakala, and Helge Lemmetyinen, *Macromolecules* (2000), 33, 438-443, and (c) Paula Bosch, Fernando Catalina, Teresa Corrales, and Carmen Peinado, *Chem. Eur. J.* (2005) 11, 4314-4325.

In the methods described in the noted Wang et al. publication and U.S. Pat. No. 4,651,011 (noted above), photocuring monitoring requires the use of soluble probe molecules that are not covalently bound to the resulting polymer, providing potential environmental and measurement problems called "probe bloom." Furthermore, such methods are sensitive to changes in concentration of the probe molecules that work well only at very low concentrations.

The noted methods have been shown to be useful as photocuring monitors only in low viscosity [less than 300 cP, reference (b) above] compositions. The method described for example in reference (b) requires the monitoring of small (10-20 nm) spectral shifts in the fluorescence spectrum of the probe molecule.

Many dibenzofulvene derivatives are known in the art, as described for example in U.S. Pat. No. 3,091,651 (Soderquist et al.), U.S. Pat. No. 5,047,444 (DeVoe et al.), and U.S. Pat. No. 3,091,652 (Soderquist et al.); and in *J. Org. Chem.* (1987), 52, 688. Furthermore, it is known that certain dibenzofulvenes are either non-fluorescent or weakly fluorescent [see H. Stegemeyer, Ber. Bunsenges, *Phys. Chem.* (1968), 72, 335-344].

U.S. Pat. No. 5,633,313 (Blanchard et al.) describes a method and apparatus for using fluorescent probe molecules (such as pyrene and oxazone) to monitor curing in thermally curable acrylate polymers, which upon curing cause a shift in the fluorescence emission spectrum from the fluorescent probe molecules.

U.S. Pat. No. 5,047,444 (Devoe et al.) describes the use of a latent dibenzofulvene-based fluorophore (probe) that is added to a release coating as a curing monitor. When subjected to the curing conditions, the monitor forms an ultraviolet radiation-detectable fluorophore that is detected by irradiation using an ultraviolet light source of a particular wavelength. The ultraviolet radiation is absorbed by the fluorophore that in turn emits radiation that can be detected by suitable photosensing apparatus. The intensity of the emission can be used to determine whether proper curing has been achieved. This kind of detection requires the use of a hard-to-control reaction of latent dibenzofulvene during polymerization to form a fluorescent detectable fluorophore that could lead to incorrect determinations of curing. Furthermore, since detection is based on the total intensity of fluorescence, it has quite limited utility for monitoring the degree of curing above the gel point (that is, it has limited dynamic range) and it is subject to uncertainty due to variations in background fluorescence. Furthermore, any variation in photocurable coating thickness will have an impact on fluorescence intensity and this also can lead to an incorrect curing determination.

Thus, there is a need to provide a simple, reliable, and economical method for determining the degree of photocuring of photocurable compositions such as acid catalyzed photocurable compositions. Moreover, there is a need for a reliable fluorescence probe for monitoring the degree of photocuring, and for use as a fluorescence monitor or probe to evaluate changes in various environments that may not include photocuring.

SUMMARY OF THE INVENTION

This invention provides a method for determining the extent of curing in a layer of a photocurable or thermally curable composition (of any embodiment described herein), the method comprising:

providing a dried layer of a photocurable or thermally curable composition over a supporting side of a transparent polymeric substrate, the dried layer having an outermost surface and an innermost surface, and the photocurable or thermally curable composition comprising a photocurable or thermally curable component and pyrene, exposing the photocurable or thermally curable composition to form an at least partially photocured or thermally cured composition in an at least partially photocured or thermally cured dried layer having an innermost surface and an outermost surface, determining a first fluorescence emission spectrum emitted by the pyrene at the innermost surface of the at least partially photocured or thermally cured dried layer, determining a second fluorescence emission spectrum emitted by the pyrene at the outermost surface of the at least partially photocured or thermally cured dried layer, comparing the first fluorescence emission spectrum and the second fluorescence emission spectrum to determine any difference in curing between the outermost surface and the innermost surface of the at least partially photocured or thermally cured dried layer.

The use of ratiometric fluorescence using a fluorescent probe molecule to evaluate chemical or physical phenomena depends upon the sensitivity of the fluorescent probe molecule to some type of change in a property of the environment into which it is placed. Two such environmental properties include polarity and structural rigidity. For best performance, it is also desirable that a fluorescent probe molecule have a large absorptivity and moderately high fluorescence quantum yield so that the change in environmental properties can be effectively measured and the data used for purposeful application.

The present invention provides a number of advantages by using ratiometric fluorescence and a fluorescent probe molecule, pyrene, which meets these expectations. Pyrene has large absorptivity (extinction coefficient ~60,000 M-1 cm-1) and can be used in the manner in small amounts, for example, at 1 weight % of less of a composition into which it is incorporated.

Pyrene has a long fluorescence lifetime (about 400 nsec in argon purged tetradecane) and a high quantum yield of emission (0.32 in cyclohexane) that is well resolved from the monomer emission, and hence is easily detectable. Pyrene does not exhibit spectral frequency shifts similar to solvatochromic molecules. Pyrene exhibits a variation in the ratio of emission band intensities that has been correlated with the polarity of the immediate environment. The empirical 'Py" scale of solvent polarity has been established based on the emission response of pyrene and has been catalogued for a wide variety of solvents. It has been shown that the ratio of $1^{st}$ peak to $3^{rd}$ peak ($I_1/I_3$) can be used to probe the polarity of the environment of pyrene (see *Can. J. Chem.* 1984, 62, 2560). An important advantage of pyrene as a fluorescent probe is that the measurement depends only upon the ratio of emission band intensities and is not dependent on the exact concentration of pyrene.

Pyrene can be used in the manner in trace amounts, for example, at 1 weight % of less of a composition into which it is incorporated. Pyrene can be used in chemical environments in which it is non-reactive with other chemical components such as polymer materials, monomeric reactants, solvents, or curing initiators that can change the properties of the chemical environment. By "non-reactive," pyrene does not adversely affect the properties of the photocurable or thermally curable composition components with which it is mixed.

The present invention provides a simple, reliable, and economical means for using ratiometric fluorescence probe techniques, for example for determining whether photocuring or thermal curing has occurred and determining the extent of photocuring or thermal curing. The methods can be used in any photocurable or thermally curable composition because the change in chemical polarity in the photocurable or thermally curable composition due to curing readily affects the peaks of fluorescent spectrum of pyrene that is used as the ratiometric fluorescent probe molecule. The present invention is particularly useful to monitor the progress of photocuring in acid-catalyzed photocurable compositions that can be used for example in continuous photocuring processes such as roll-to-roll processes used to make a continuous web with conductive elements produced at least in part from the photocuring.

In addition, pyrene can be used as a "fluorescent probe" to determine the level of (or loss of) one or more organic solvents in various compositions including photocurable or thermally curable compositions ("inks"). The loss in organic solvents can occur from evaporation during formulation or use. Thus, detection of a change in fluorescent spectra emitted from pyrene (for example, changes in fluorescent spectral peaks) in the photocurable or thermally curable compositions can tell an operator whether more organic solvent needs to be added in a replenishing process or if other conditions of the photocurable or thermally curable composition have changed.

In still other embodiments, pyrene can be used as a ratiometric fluorescent probe to detect the difference in curing between opposing surfaces of either a photocured or thermally cured layer on a substrate.

In some other embodiments, pyrene can be provided in the photocurable or thermally curable compositions can serve multiple purposes. For example, it can be used as a photosensitizer in certain photocuring reactions as well as serving as a "fluorescent probe" as noted above.

These and other benefits from the present invention can be understood from the details provided below particularly in view of which would be known to one skilled in the art.

DETAILED DESCRIPTION OF THE INVENTION

Figure 1:
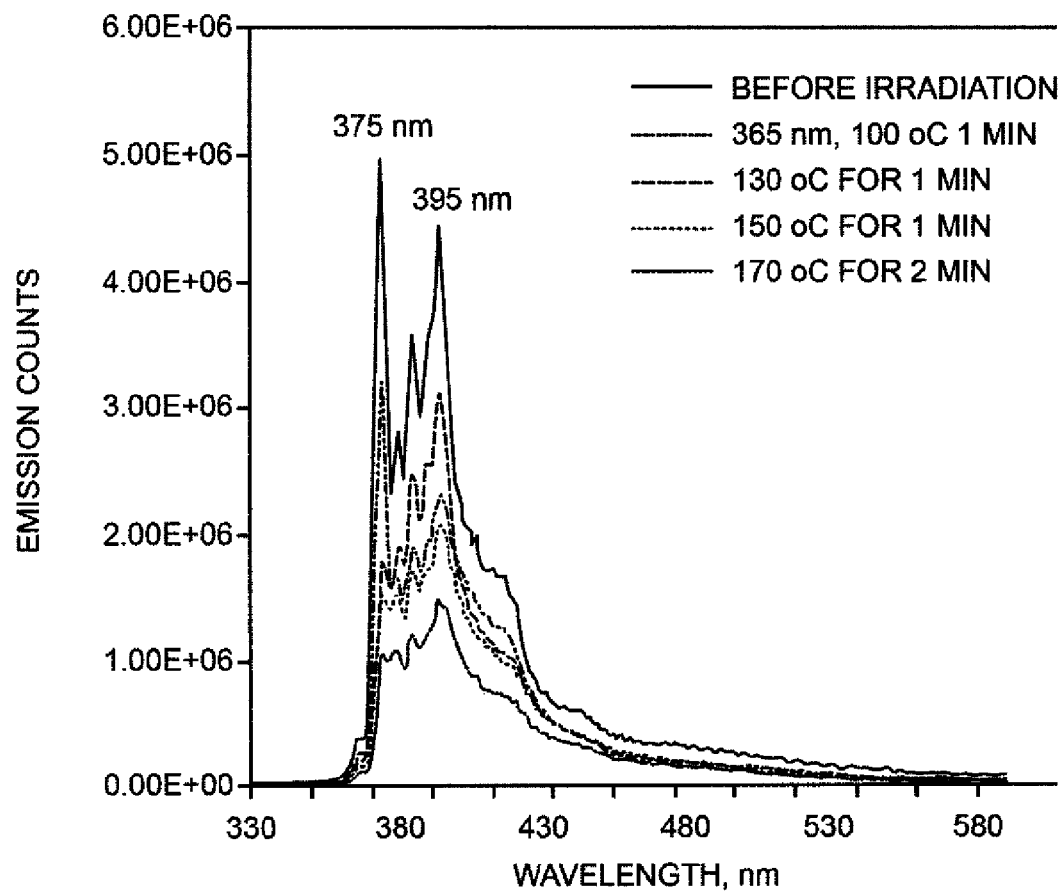
FIG. 1 is a fluorometric spectrum showing results of fluorometric emissions described in Invention Example 1 below.

The following discussion is directed to various embodiments of the present invention and while some embodiments can be particularly desirable for specific uses, the disclosed embodiments should not be interpreted or otherwise considered to limit the scope of the present invention, as claimed below. In addition, one skilled in the art will understand that the following disclosure has broader application than is explicitly described and the discussion of any embodiment is not intended to limit the scope of the present invention.

DEFINITIONS

As used herein to define various components of photocurable or thermally curable compositions, unless otherwise indicated, the singular forms "a," "an," and "the" are intended to include one or more of the components (that is, including plurality referents).

Each term that is not explicitly defined in the present application is to be understood to have a meaning that is commonly accepted by those skilled in the art. If the construction of a term would render it meaningless or essentially meaningless in its context, the term definition should be taken from a standard dictionary.

The use of numerical values in the various ranges specified herein, unless otherwise expressly indicated otherwise, are considered to be approximations as though the minimum and maximum values within the stated ranges were both preceded by the word "about." In this manner, slight variations above and below the stated ranges can be used to achieve substantially the same results as the values within the ranges. In addition, the disclosure of these ranges is intended as a continuous range including every value between the minimum and maximum values.

As used herein, all molecular weights are weight average molecular weights that can be determined using known procedures and equipment if the values are not already known from the literature.

Unless otherwise indicated, the term "photocurable composition" refers to compositions that are useful in the practice of the various methods of the present invention, which compositions have at least one component that can be cured, polymerized, or reacted using exposure to suitable ultraviolet or visible (actinic) radiation ("photoexposure") typically having a wavelength of at least 150 nm and up to and including 700 nm.

Unless otherwise indicated, the term "thermally curable composition" refers to compositions that are useful in the practice of the various methods of the present invention, which compositions have at least one component that can be cured, polymerized, or reacted using heat, near-infrared radiation, or infrared radiation (typically having a wavelength greater than 700 nm)

The term "curing" is used herein to mean the combining, for example by covalent bonding, of a large number of smaller molecules (such as monomers) to form large molecules, that is, macromolecules or polymers. The monomers can be combined to form only linear macromolecules or they can be combined to form three-dimensional macromolecules that are commonly referred to as crosslinked polymers. A type of curing carried out in the practice of some embodiments of this invention is acid-catalyzed (cationic) polymerization, but free radical polymerization can also occur in curable compositions if optional free radically polymerizable materials and suitable free radical generating photoinitiators are also present. In many useful embodiments, both acid-catalyzed curing (or polymerization) and free radically curing (or polymerization) can occur simultaneously. Curing can also include polymerization of unsaturated monomers or oligomers in the presence of crosslinking agents.

Average dry thickness of layers described herein can refer to the average of at least 2 separate measurements of the dry layer taken, for example, using electron microscopy.

Similarly, the average dry thickness or width of lines, grid lines, or other pattern features described herein can be the average of at least 2 separate measurements taken, for example, using electron microscopy. Average width of a line is generally considered to be from one outer edge to the other outer edge.

The term "supporting side" refers to the planar side of a substrate or support material on which a material can be disposed, as opposed to a non-supporting edge of a substrate or support.

The term "polymerizable epoxy material" is meant to include any material or compound having one or more oxirane rings that are capable of undergoing polymerization. This term encompasses epoxy-containing monomers, epoxy-containing oligomers, and epoxy-containing crosslinking agents. The singular form of the term is intended to include the plural form of the term. Oligomeric and multifunctional epoxy materials are also useful polymerizable epoxy materials.

The term "electron donor photosensitizer" is meant to refer to a light absorbing compound used to induce photocuring. Upon photoexcitation, the electron donor photosensitizer leads to one-electron reduction of the onium salt.

The term "photoinitiator" is meant to refer to an "onium salt" or an "onium compound" or other photoacid generator that is capable of accepting an electron from an excited electron donor photosensitizer, a process that leads to fragmentation of the onium salt to provide a Brönsted acid that initiates polymerization of the epoxy material.

The term "visible light" is used herein to refer to electromagnetic radiation having a wavelength ($\lambda_{max}$) of greater than 400 nm to and up to and including 700 nanometers (nm).

The term "UV light" is used herein to refer to electromagnetic radiation having a wavelength ($\lambda_{max}$) of at least 150 nm and up to and including 400 nm.

Near-infrared radiation and infrared radiation are used herein to refer to electromagnetic radiation having a wavelength ($\lambda_{max}$) that is greater than 700 nm.

Uses

The methods described herein can be used for a variety of purposes where efficient curing is needed to form articles or devices wherein there is a need to monitor the progress of any photocuring or thermal curing, or another change in the chemical environment of an organic mixture. Photocurable or thermally curable compositions used in the present invention are not particularly limited but some highly desirable photocurable compositions (described below) can be used to provide electrically-conductive metal patterns, for example using electroless plating procedures, which can be incorporated into various devices including but not limited to touch screen or other display devices for numerous industrial and commercial purposes.

The present invention can be used in various methods that utilize these photocurable or thermally curable compositions in order to provide quality control of the various industrial processes in the preparation of such display devices.

Touch screen technology can comprise different touch sensor configurations including capacitive and resistive touch sensors. Resistive touch sensors comprise several layers that face each other with a gap between adjacent layers that may be preserved by spacers formed during manufacturing. When an object such as a stylus, palm, or fingertip presses down on a point on the panel outer surface, the two metallic layers come into contact and a connection is formed that causes a change in the electrical current. This touch event is sent to a controller for further processing.

Capacitive touch sensors can be used in electronic devices with touch-sensitive features such that human touch of the touch region of the device changes the capacitance of an electrically-conductive metal grid or pattern. These electronic devices can include but are not limited to, televisions, monitors, and projectors that can be adapted to display images including text, graphics, video images, movies, still images, and presentations. The image devices that can be used for these display devices that can include cathode ray tubes (CRS's), projectors, flat panel liquid crystal displays (LCD's), LED systems, OLED systems, plasma systems, electroluminescent displays (ECD's), and field emission displays (FED's). For example, the present invention can be used to prepare capacitive touch sensors that can be incorporated into electronic devices with touch-sensitive features to provide computing devices, computer displays, automated teller machines, portable media players including e-readers, mobile telephones and other communicating devices.

Systems and methods of fabricating flexible and optically compliant touch sensors in a high-volume roll-to-roll manufacturing process where micro electrically conductive features can be created in a single pass are possible using the present invention. Photocurable compositions can be used in such systems and methods with multiple printing members such as multiple flexographic printing plates to form multiple high resolution electrically-conductive images from predetermined designs of patterns provided in those multiple printing members. Multiple patterns can be printed on one or both supporting sides of a substrate as described in more details below. For example, one predetermined pattern can be printed on one supporting side of the substrate and a different predetermined pattern can be printed on the opposing supporting side of the substrate. The printed patterns of photocurable or thermally curable compositions can then be cured and further processed to provide electrically-conductive metal patterns such as for example using electroless metal plating. In all of these processes, pyrene can be used as a suitable fluorescent probe to monitor curing or other composition chemical changes.

Thermally Curable Compositions

Various thermally-curable compositions can be used in the practice of this invention, which compositions generally include a thermally-curable component such as thermally-curable epoxy compounds and a suitable catalyst such as primary and secondary amines, anhydrides, phenols, thiols, carboxylic acids, and combinations thereof (for example see Auvergne et al Chem. Rev. 2014, 114, 1082).

Various thermally curable polymers and compositions are known. For example, thermal initiation of polymerization of cyclic ethers is known from for example, J. V. Crivello, et al. *J. Polym. Sci.: Part A: Polym Chem.*, Vol. 27, pp 3951-3968 (1989) and J. V. Crivello, et al., *J. Polym. Sci.: Polym. Chem, Ed.*, Vol. 21, pp 97-109 (1983). U.S. Pat. No. 4,173,551 (Crivello) describes thermally curable epoxy compositions comprising a cationically polymerizable organic material, such as an epoxy resin, and an effective amount of a diaryliodonium salt used in combination with a co-catalyst such as a copper salt, an organic acid, or mixtures thereof.

Of the many thermally curable resins, including phenolic resins, urea-aldehyde resins, urethane resins, melamine resins, epoxy resins, and alkyd resins, phenolic resins are used extensively to manufacture abrasive articles because of their thermal properties, availability, low cost, and ease of handling. Such phenolic resins are cured by further reaction with formaldehyde or formaldehyde-producing compounds and/or by the residual methylol groups in the resin. U.S. Pat. No. 3,267,053 (Nagle et al.) provides examples of thermally cured phenol-aldehyde resin compositions.

High temperature stable polymers, particularly polyimides, are well-known in the microelectronics industry and can be used as insulators, interlevel dielectrics, and passivation layers for various types of metallurgy. Polyimides are useful instead of inorganic insulators because they generally have a lower dielectric constant, are more amenable to film processing, and encompass a wide variety of chemistries that can be chosen to meet the functional requirements for different applications. Polyimides are generally prepared either through direct condensation reactions to afford linear, long chain, polyimides, or through addition reactions performed on end-capped imide oligomers to give crosslinked polyimides. For example, U.S. Pat. No. 3,745,149 (Serafini et al.) and U.S. Pat. No. 3,528,950 (Lubowitz) disclose methods for preparing such polyimides.

Other polymer materials that can be cured thermally are polyurethanes or polyureas that are produced by reacting diols or diamines with di- or multiisocyanates (cf. H.-G. Elias, *Makromolekule*, Volume 2, page 225, H uthig & Wepf Verlag, Basel, Heidelberg, N.Y. 1992).

U.S. Pat. No. 4,408,018 (Bartman et al.) and U.S. Pat. No. 5,017,649 (Clemens) describe polymers having acetoacetate or acrylate groups that can be crosslinked by Michael reaction with di- or polyfunctional acrylates and acetoacetates, respectively. According to R. J. Clemens, F. Del Rector, *J. Coating Techn.* 61, 83 (1989) such crosslinked polymers can be used as paints, which however showed only a slight resistance to hydrolysis. The accepted reason for this disadvantage is that the amidine base used catalyses the hydrolysis of the crosslinked film in the finished coating.

The pyrene fluorescent probe can be incorporated into any of these thermally-curable compositions according to the present invention to carry out the methods described herein in a suitable amount as described below.

Photocurable Compositions

Various photocurable compositions can be used in the practice of the present invention as long as pyrene is included in a suitable amount (described below) so that desired fluorescence emission spectra can be produced, detected and compared as described herein. Such photocurable compositions comprise one or more photocurable components that can be polymerized or cured in a suitable manner.

For example, some useful photocurable compositions include but are not limited to, free radical photocurable compositions and acid-catalyzed photocurable compositions (such as epoxy-containing compositions) containing pyrene as a suitable fluorescent probe as described herein in amounts that are similar to the amounts described below.

In some embodiments of this invention, the photocurable compositions are sensitive throughout the UV to visible spectral region as described above and are photocurable in these electromagnetic regions without appreciable application of heat. Thus, photocuring or photopolymerization can occur at essentially room temperature (for example, as low as 18° C.) when all of the components are properly mixed together. Photopolymerization [either or both acid catalysis and free radical polymerization] then readily takes place upon suitable exposure to a source of suitable radiation to initiate the various chemical reactions that are required.

Photocurable Compositions-Class I:

Photocurable compositions of this class are designed to be have only four essential components (a) through (d) described herein, which are the only components necessary for photocuring. Optional addenda can also be included as described below as components (e) through (g).

(a) Photopolymerizable Epoxy Materials

The cationically polymerizable epoxy materials are organic compounds having at least one oxirane ring, which oxirane ring is shown in the following formula:

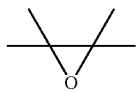

that is polymerizable by a ring opening mechanism. Such epoxy materials, also called "epoxides," include monomeric epoxy compounds and epoxides of the polymeric type and can be aliphatic, cycloaliphatic, aromatic or heterocyclic. These materials generally have, on the average, at least one polymerizable epoxy group per molecule, or typically at least about 1.5 and even at least about 2 polymerizable epoxy groups per molecule. Polymeric epoxy materials include linear polymers having terminal epoxy groups (for example, a diglycidyl ether of a polyoxyalkylene glycol), polymers having skeletal (backbone) oxirane units (for example, polybutadiene polyepoxide), and polymers having pendant epoxy groups (for example, a glycidyl methacrylate polymer or copolymer).

The polymerizable epoxy materials can be single compounds or they can be mixtures of different epoxy materials containing one, two, or more epoxy groups per molecule. The "average" number of epoxy groups per molecule is determined by dividing the total number of epoxy groups in the epoxy material by the total number of epoxy-containing molecules present.

The epoxy materials can vary from low molecular weight monomeric materials to high molecular weight polymers and they can vary greatly in the nature of the backbone and substituent (or pendant) groups. For example, the backbone can be of any type and substituent groups thereon can be any group that does not substantially interfere with cationic photocuring process desired at room temperature. Illustrative of permissible substituent groups include but are not limited to, halogens, ester groups, ethers, sulfonate groups, siloxane groups, nitro groups, and phosphate groups. The molecular weight of the epoxy materials can be at least 58 and up to and including 100,000, or even higher.

Useful epoxy materials include those that contain cyclohexene oxide groups such as epoxycyclohexane carboxylates, such as 3,4-epoxycyclohexylmethyl-3,4-epoxycyclohexane carboxylate, 3,4-epoxy-2-methylcyclohexylmethyl-3,4-epoxy-2-methylcyclohexane carboxylate, and bis(3,4-epoxy-6-methylcyclohexylmethyl) adipate. A more detailed list of useful epoxy materials of this nature is provided in U.S. Pat. No. 3,117,099 (Proops et al.).

Still other useful epoxy materials include glycidyl ether monomers that are glycidyl ethers of polyhydric phenols obtained by reacting a polyhydric phenol with an excess of a chlorohydrin such as epichlorohydrin [for example, the diglycidyl ether of 2,2-bis-(2,3-epoxypropoxyphenol)-propane]. Further examples of epoxy materials of this type are described in U.S. Pat. No. 3,018,262 (Schroeder) and in "Handbook of Epoxy Resins" by Lee and Neville, McGraw-Hill Book Co., New York (1967).

Many commercially available epoxy materials are useful in the present invention, glycidyl ethers such as bisphenol-A-diglycidyl ether (DGEBA), glycidyl ethers of bisphenol S and bisphenol F, butanediol diglycidyl ether, bisphenol-A-extended glycidyl ethers, phenol-formaldehyde glycidyl ethers (epoxy novolacs) and cresol-formaldehyde glycidyl ethers (epoxy cresol novolacs), epoxidized alkenes such as 1,2-epoxyoctane, 1,2,13,14-tetradecane diepoxide, 1,2,7,8-octane diepoxide, octadecylene oxide, epichlorohydrin, styrene oxide, vinyl cyclohexene oxicyclohexene oxide, glycidol, glycidyl methacrylate, diglycidyl ether of Bisphenol A (for example, those available under the EPON trademark such as Epon™ 828, Epon™ 825, Epon™ 1004, and Epon™ 1010 from Momentive, DER-331, DER-332, and DER-334 resins from Dow Chemical Co.), vinyl cyclohexene dioxide (for example, ERL-4206 resin from Polyscience), 3,4-epoxycyclohexylmethyl-3,4-epoxycyclohexene carboxylate (for example, ERL-4221, UVR 6110, or UVR 6105 resin from Dow Chemical Company), 3,4-epoxy-6-methylcyclohexyl-methyl-3,4-epoxy-6-methyl-cyclohexene carboxylate (from Pfalz and Bauer), bis(3,4-epoxy-6-methylcyclohexylmethyl) adipate, bis(2,3-epoxy-cyclopentyl) ether, aliphatic epoxy modified with polypropylene glycol, dipentene dioxide, epoxidized polybutadiene (for example, Oxiron 2001 resin from FMC Corp.), silicone resin containing epoxy functionality, flame retardant epoxy resins (for example, DER-580 resin, a brominated bisphenol type epoxy resin available from Dow Chemical Co.), 1,4-butanediol diglycidyl ether of phenol formaldehyde novolak (for example, DEN-431 and DEN-438 resins from Dow Chemical Co.), resorcinol diglycidyl ether (for example, CYRACURE™ resin from Dow Corning Corp.), 2-(3,4-epoxycyclohexyl-5,5-spiro-3,4-epoxy)cyclohexane-meta-dioxane, 2-(3,4-epoxycyclohexyl-5,5-spiro-3,4-epoxy)cyclohexane-meta-dioxane, vinyl cyclohexene monoxide, 1,2-epoxyhexadecane (for example, CYRACURE™ resin from Dow Corning Corp.), alkyl glycidyl ethers such as HELOXY™ Modifier 7 and HELOXY™ Modifier 8 (from Momentive), butyl glycidyl ether (for example, HELOXY™ Modifier 61 from Momentive), cresyl glycidyl ether (for example, HELOXY™ Modifier 62 from Momentive), p-tert butylphenyl glycidyl ether (for example, HELOXY™ Modifier 65 from Momentive), polyfunctional glycidyl ethers such as diglycidyl ether of 1,4-butanediol (for example, HELOXY™ Modifier 67 from Momentive), diglycidyl ether of neopentyl glycol (for example, HELOXY™ Modifier 68 from Momentive), diglycidyl ether of cyclohexanedimethanol (for example, HELOXY™ Modifier 107 from Momentive), trimethylol ethane triglycidyl ether (for example, HELOXY™ Modifier 44 from Momentive), trimethylol propane triglycidyl ether (for example, HELOXY™ Modifier 48 from Momentive), polyglycidyl ether of an aliphatic polyol (for example, HELOXY™ Modifier 84 from Momentive), polyglycol diepoxide (for example, HELOXY™ Modifier 32 from Momentive), bisphenol F epoxides (for example, EPN-1138 or GY-281 resin from Huntman Advanced Materials), and 9,9-bis>4-(2,3-epoxypropoxy)-phenyl fluorenone (for example, Epon™ 1079 resin from Momentive).

Still other useful epoxy materials are resins such as copolymers derived from acrylic acid esters reacted with glycidol such as glycidyl acrylate and glycidyl methacrylate, copolymerized with one or more ethylenically unsaturated polymerizable monomers. Other useful epoxy materials are epichlorohydrins such as epichlorohydrin, alkylene oxides such as propylene oxide and styrene oxide, alkenyl oxides such as butadiene oxide, and glycidyl esters such as ethyl glycidate.

Still other useful epoxy materials are silicones having an epoxy functionality or group such as cyclohexylepoxy groups, especially those epoxy materials having a silicone backbone. Commercial examples of such epoxy materials include UV 9300, UV 9315, UV 9400, UV 9425 silicone materials that are available from Momentive.

Polymeric epoxy materials can optionally contain other functionalities that do not substantially interfere with cationic photocuring of the photocuring composition at room temperature. For example, the photopolymerizable epoxy materials can also include free-radical polymerizable functionality.

The photopolymerizable epoxy material can comprise a blend or mixture of two or more different epoxy materials. Examples of such blends include two or more molecular weight distributions of photopolymerizable epoxy materials.

The photopolymerizable epoxy materials can be used to provide binder function if desired for given utilities. Otherwise, non-photocurable polymers or resins can be included for this purpose if needed. Alternatively, the photocurable acrylates described below can be used to provide a binder function.

One or more photopolymerizable epoxy materials are included in the photocurable composition in a suitable amount, for example, in an amount of at least 10 weight % and up to and including 95 weight %, or typically of at least 50 weight % and up to and including 75 weight %, based on the total solids in the photocurable composition.

(b) Photoacid Generators

Various compounds can be used to generate a suitable acid to participate in the photocuring described herein. Some of these "photoacid generators" are acidic in nature and others are nonionic in nature. The various compounds useful as photoacid generators can be purchased from various commercial sources or prepared using known synthetic methods and starting materials.

Onium salt acid generators useful in the practice of this invention include but are not limited to, salts of diazonium, phosphonium, iodonium, or sulfonium salts including polyaryl diazonium, phosphonium, iodonium, and sulfonium salts. The iodonium or sulfonium salts include but not limited to, diaryliodonium and triarylsulfonium salts. Useful counter anions include but are not limited to complex metal halides, such as tetrafluoroborate, hexafluoroantimonate, trifluoromethanesulfonate, hexafluoroarsenate, hexafluorophosphate, and arenesulfonate. The onium salts can also be oligomeric or polymeric compounds having multiple onium salt moieties as well as molecules having a single onium salt moiety.

Other suitable iodonium salts include those described in U.S. Pat. No. 5,545,676 (Palazzotto et al.) at column 2 (lines 28 through 46); U.S. Pat. No. 3,729,313 (Smith); U.S. Pat. No. 3,741,769 (Smith); U.S. Pat. No. 3,808,006 (Smith); U.S. Pat. No. 4,250,053 (Smith); and U.S. Pat. No. 4,394,403 (Smith), the disclosures of which are incorporated herein by reference.

Useful iodonium salts can be simple salts (for example, containing an anion such as chloride, bromide, iodide, or $C_4H_5SO_3^-$) or a metal complex salt (for example, containing $SbF_6^-$, $PF_6^-$, $BF_4^-$, tetrakis(perfluorophenyl)borate, or $SbF_5OH_{31} AsF_6^-$).

Sulfonium salts are desirable for use and should be soluble in any inert organic solvents (described below) and they should also be shelf-stable, meaning they do not spontaneously promote polymerization when mixed with the other components especially the electron acceptor photosensitizer and electron donor co-initiator prior to exposure to suitable radiation.

Particularly useful sulfonium salts include but are not limited to, triaryl-substituted salts such as mixed triarylsulfonium hexafluoroantimonates (for example, commercially available as UVI-6974 from Dow Chemical Company), mixed triarylsulfonium hexafluorophosphates (for example, commercially available as UVI-6990 from Dow Chemical Company), and arylsulfonium hexafluorophosphates (for example, commercially available as SarCa™ KI85 from Sartomer Company).

One or more onium salts (such as an iodonium salt or a sulfonium salt) are generally present in the photocurable composition in an amount of at least 0.05 weight % and up to and including 10 weight %, or typically at least 0.1 weight % and up to and including 10 weight %, based on the total solids in the photocurable composition.

Besides onium salts described above, nonionic photoacid generators are also useful in present invention, which include but are not limited to, diazomethane derivatives, glyoxime derivatives, bis-sulfone derivatives, disulfono derivatives, nitrobenzyl sulfonate derivatives, sulfonic acid ester derivatives, and sulfonic acid esters of N-hydroxyimides.

(c) Pyrene is the only compound used as a fluorescence probe for the photocurable compositions. It is generally present in an amount of at least 0.0001 weight % and up to and including 10 weight %, or more likely in an amount of at least 0.2 weight % and up to and including 1 weight %, all based on the total solids in the photocurable composition.

(d) Organic Solvents

The photocurable compositions are generally provided in a suitable organic diluent that serves as a non-aqueous (organic) solvent or combination of solvents in which the components of the photocurable composition are dissolved or dispersed. In many embodiments, the organic diluent is an organic solvent medium that includes one or more inert organic solvents such as 2-ethoxyethanol, 2-(2-methoxyethoxy)ethanol, 2-(2-ethoxyethoxy)ethanol, 1-methoxy-2-propanol (Dowanol PM), 4-heptanone, 3-heptanone, 2-heptanone, cyclopentanone, cyclohexanone, diethyl carbonate, 2-ethoxyethyl acetate, N-butyl butyrate, acetone, dichloromethane, isopropanol, ethylene glycol, and methyl lactate. Mixtures of these listed inert organic solvents can be used in the organic solvent medium in any suitable volume or weight ratio. Other useful organic solvents could be readily identified by one skilled in the art using the teaching provided herein. By "inert," it is meant that the organic solvents do not appreciably participate in any chemical reactions.

The organic diluent (such as the organic solvent medium) can provide up to and including 1 weight %, or up to at least 70 weight % or at least 10 weight % and up to and including 30 weight %, based on the total weight of the photocurable composition. The amount of inert organic solvents can be judiciously chosen depending upon the particular materials used, the means for applying the resulting photocurable composition, and desired properties including composition uniformity.

When one or more photocurable components (as described above) are present as liquid organic compounds, those one or more photocurable components can act as the organic diluent and separate inert organic solvents may not be necessary. In such instances, the organic diluent can be considered a "reactive" diluent. Alternatively, one or more reactive diluents can be used combination with one or more inert organic solvents to form a suitable organic diluent.

(e) Metal Particles

Metal particles can be present in the photocurable composition. Usually only one type of metal particles are used, but it is also possible to include mixtures of different metal particles, from the same or different classes of metals, that do not interfere with each other. These metal particles generally have a net neutral charge.

Useful metal particles can be chosen from one or more classes of noble metals, semi-noble metals, Group IV metals, or combinations thereof. Useful noble metal particles include but are not limited to, particles of gold, silver, palladium, platinum, rhodium, iridium, rhenium, mercury, ruthenium, and osmium. Useful particles of semi-noble metals include but are not limited to, particles of iron, cobalt, nickel, copper, carbon, aluminum, zinc, and tungsten. Useful particles of Group IV metals include but are not limited to particles of tin, titanium, and germanium. The noble metal particles such as particles of silver, palladium, and platinum are particularly useful, and the semi-noble particles of nickel and copper are also particularly useful. Tin particles are particularly useful in the Group IV metal class. In many embodiments, silver or copper particles are used in the photocurable composition.

The metal particles can be coated isolated using surfactants, polymers, or carbon. The carbon on coated metal particles can be amorphous, sp2 hybridized, or graphene-like in nature. Such carbon can be used to prevent aggregation of metal particles and provide improved dispersibility in the photocurable composition.

The metal particles can be dispersed in various organic solvents and can have improved dispersibility in the presence of the other components of the photocurable composition, such as multifunctional polymeric epoxy materials or in the presence of components such as multifunctional acrylate resins described below. The methods used to disperse the metal particles include but are not limited to, ball-milling, magnetic stirring, high speed homogenization, high pressure homogenization, and ultrasonication.

The metal particles can be present in the photocurable composition as individual particles, but in many embodiments, the metal particles are present as agglomerations of two or more metal particles. Such metal particles can be present in any geometric shape including but not limited to, spheres, rods, prisms, cubes, cones, pyramids, wires, flakes, platelets, and combinations thereof, and they can be uniform or non-uniform in shapes and sizes. The average particle size of individual and agglomerated metal particles can vary from at least 0.01 µm and up to and including 25 µm, or more likely of at least 0.02 µm and up to and including 5 µm. Although the size of the metal particles is not particularly limited, optimal benefits can be achieved using metal particles as individual particles or agglomerates, having an average particle size of at least 0.02 µm and up to and including 10 µm. The particle size distribution is desirably narrow as defined as one in which greater than 50%, or typically at least 75%, of the particles have a particle size in the range of 0.2 to 2 times the average particle size. The average particle size (same as mean particle size) can be determined from the particle size distribution that can be determined using any suitable procedure and equipment including that available from Coulter or Horiba and the appropriate mathematical calculations used with that equipment.

Useful metal nanoparticles can be obtained from various commercial sources, or they can be derived from various metal salts or complexes and known reduction and isolation processes prior to use in the practice of this invention. Some commercial metal particles can be obtained for example from NovaCentrix (Austin, Tex.).

The metal particles can be generally present in the photocurable composition in an amount of at least 0.1 weight % and up to and including 50 weight % or more typically at least 1 weight % and up to and including 30 weight %, based on the total solids in the photocurable composition.

(f) Free Radically Polymerizable Compounds

The photocurable compositions can also contain one or more free-radically polymerizable compounds to provide free-radically polymerizable functionality, including ethylenically unsaturated polymerizable monomers, oligomers, or polymers such as mono-functional or multi-functional acrylates (also includes methacrylates). Such free-radically polymerizable compounds comprise at least one ethylenically unsaturated polymerizable bond and they can comprise two or more of these unsaturated moieties in many embodiments, which moieties can be reacted in the presence of free radicals. Suitable materials of this type contain at least one ethylenically unsaturated polymerizable bond and are capable of undergoing addition (or free radical) polymerization. Such free radically polymerizable materials include mono-, di-, or poly-acrylates and methacrylates including but not limited to, methyl acrylate, methyl methacrylate, ethyl acrylate, isopropyl methacrylate, n-hexyl acrylate, stearyl acrylate, allyl acrylate, glycerol diacrylate, glycerol triacrylate, ethylene glycol diacrylate, diethylene glycol diacrylate, triethylene glycol dimethacrylate, 1,3-propanediol diacrylate, 1,3-propanediol dimethacrylate, 1, 4-butanediol diacrylate, 1,6-hexanediol diacrylate, neopentyl glycol diacrylate, neopentyl glycol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, dipentaetrythritol hexaacrylate, sorbitol hexaacrylate, bis[1-(2-acryloxy)]-p-ethoxyphenyldimethylmethane, bis[1-(3-acryloxy-2-hydroxy)]-p-propoxyphenyldimethylmethane, and tris-hydroxyethyl-isocyanurate trimethacrylate; the bis-acrylates and bis-methacrylates of polyethylene glycols having a molecular weight of from 200 to and including 500, co-polymerizable mixtures of acrylate monomers such as those described in U.S. Pat. No. 4,652,274 (Boettcher et al.) and acrylate oligomers such as those described in U.S. Pat. No. 4,642,126 (Zader et al.); and vinyl compounds such as styrene and styrene derivatives, diallyl phthalate, divinyl succinate, divinyl adipate, and divinyl phthalate. Mixtures of two or more of these free radically polymerizable materials can be used if desired.

Such materials can be purchased from a number of commercial sources or prepared using known synthetic methods and starting materials.

Although the amount of the one or more free radically polymerizable materials is not particularly limited, they can be present in the photocurable compositions in an amount of at least 20 weight % and up to and including 75 weight % or typically of at least 40 weight % and up to and including 60 weight %, based on the total solids of the photocurable composition and can be optimized based on the desired properties of composition solubility and mechanical strength of the photocured composition.

(g) Free Radical Photoinitiators

If the component (f) is present, one or more free radical photoinitiators are also generally present in the photocurable compositions to generate free radicals in the presence of the free-radically polymerizable compounds. Such free radical photoinitiators can include any compound that is capable of generating free radicals upon exposure to photopolymerizing radiation used in the practice of this invention such as ultraviolet or visible radiation. For example, free radical photoinitiators can be selected from triazine compounds, thioxantone compounds, benzoin compounds, carbazole compounds, diketone compounds, sulfonium borate compounds, diazo compounds, and biimidazole compounds, and others that would be readily apparent to one skilled in the art. Mixtures of such compounds can be selected from the same or different classes.

Also useful are benzophenone compounds such as benzophenone, benzoyl benzoate, methyl benzoyl benzoate, 4-phenyl benzophenone, hydroxyl benzophenone, acrylated benzophenone, 4,4'-bis(dimethylamino)benzophenone and 4,4'-bis(diethylamino)benzophenone, anthraquinone compounds, and acetophenone compounds such as 2,2'-diethoxyacetophenone, 2,2'-dibutoxyacetophenone, 2-hydroxy-2-methylpropiophenone, p-t-butyltrichloroacetophenone, p-t-butyldichloroacetophenone, benzophenone, 4-chloroacetophenone, 4,4'-dimethylaminobenzophenone, 4,4'-dichlorobenzophenone, 3,3'-dimethyl-2-methoxybenzophenone, 2,2'-dichloro-4-phenoxyacetophenone, 2-methyl-1-(4-(methylthio)phenyl)-2-morpholinopropan-1-one, and 2-benzyl-2-dimethylamino-1-(4-morpholinophenyl)-butane-1-one. Further useful compounds of this type are described for example in U.S. Pat. No. 7,875,416 (Park et al.).

Many of such free radical photoinitiators can be obtained from various commercial sources.

Such free radical photoinitiators are generally present in the photocurable composition in an amount of at least 0.1 weight % and up to and including 10 weight %, or typically at least 1 weight % and up to and including 5 weight %, based on the total solids of the photocurable composition.

Photocurable Compositions—Class II:

Another class of useful photocurable compositions comprises:
(a) a photopolymerizable epoxy material,
(b) a photoacid generator,
(c) pyrene,
(d) an organic diluent,
(e) an electron acceptor photosensitizer,
(f) an electron donor co-initiator having an oxidation potential of 0.1 V to 3 V vs. SCE,
(g) metal particles,
(h) optionally, a free radically polymerizable compound, and
(i) optionally, a free radical generating photoinitiator.

Components (a), (b), (c), (d), (g), (h), and (i) and their useful amounts are described above, wherein component (g) metal particles are described above as component (e), component (h) free radically polymerizable compounds are described above as component (f), and component (i) free radical generating photoinitiators are described above as component (g).

The other useful components are described as follows.

(e) Electron Acceptor Photosensitizers

Useful electron acceptor photosensitizers should be soluble in the photocurable composition, free of functionalities that would substantially interfere with the cationic photocuring process, and capable of light absorption (sensitivity) within the range of wavelengths of at least 150 nm and up to and including 1000 nm.

Suitable photosensitizers initiate the chemical transformation of the onium salt in response to the photons absorbed from the irradiation. The photosensitizer should also be capable of oxidizing the electron donor co-initiator (described below) to a radical cation after the photosensitizer has absorbed light (that is, photoinduced electron transfer). Thus, the electron acceptor photosensitizer, upon absorption of photons from irradiation, is generally capable of accepting an electron from the electron donor co-initiator.

For uses of the photocurable compositions in which very rapid curing (such as the curing of thin applied films of the compositions) is desired, the electron acceptor photosensitizers can have an extinction coefficient of at least 1000 liter-mole$^{-1}$ cm$^{-1}$ and typically at least 10,000 liters-mole$^{-1}$ cm$^{-1}$ at the desired irradiation wavelength using the photocuring process.

In general, many different classes of compounds can be used as electron acceptor photosensitizers for various reactants, provided that the energetic requirements discussed above are satisfied. Useful photosensitizers include but are not limited to, cyanoaromatics such as 1-cyanonaphthalene, 1,4-dicyanonaphthalene, 9,10-dicyanoanthracene, 2,9,10-tricyanoanthracene, 2,6,9,10-tetracyanoanthracene; aromatic anhydrides and imides such as 1,8-naphthylene dicarboxylic, 1,4,6,8-naphthalene tetracarboxylic, 3,4-perylene dicarboxylic, and 3,4,9,10-perylene tetracarboxylic anhydride or imide; condensed pyridinium salts such as quinolinium, isoquinolinium, phenanthridinium, acridinium, and pyrylium salts.

Other useful electron acceptor photosensitizers that involve the triplet excited state are carbonyl compounds such as quinones such as benzo-, naphtho-, anthro-quinones having electron withdrawing substituents (such as chloro and cyano). Ketones including aromatic ketones such as fluorenone, and coumarin dyes such as ketocoumarins such as those with strong electron withdrawing moieties (such as pyridinium) can also be used as electron acceptor photosensitizers. Other suitable electron acceptor photosensitizers are believed to include xanthene dyes, acridine dyes, thiazole dyes, thiazin dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Diarylketones and other aromatic ketones such as fluorenone are useful electron acceptor photosensitizers.

Various useful electron acceptor photosensitizers are available from various commercial sources and can be readily found for use in the present invention.

The one or more electron acceptor photosensitizers can be present in the photocurable composition in an amount of at least 0.0001 weight % and up to and including 5 weight %, and typically at least 0.001 weight % and up to and including 2 weight %, based on total solids of the photocurable composition.

(f) Electron Donor Co-Initiators

These components can be the same as those compounds defining component (e) above as "electron donor photosensitizer", but do not include pyrene. However for the Class II photocurable compositions, these electron donor co-initiators generally have an oxidation potential of 0.1 V to and including 3 V vs. SCE.

Photocurable Compositions—Class III:

Still another class of photocurable compositions useful in the practice of this invention can comprise the following components:

(a) a photopolymerizable epoxy material,
(b) a photoacid generator,
(c) pyrene
(d) an organic diluent,
(e) an electron donor photosensitizer other than pyrene, which electron donor photosensitizer has an oxidation potential of at least 0.4 V and up to and including 3 V vs. SCE,
(f) metal particles,
(g) optionally, a free-radically polymerizable compound, and
(h) optionally, a free radical generating photoinitiator.

In these photocurable compositions, components (a), (b), (c), (d), (f), (g), and (h) and useful amounts are described above except component (f) is described above as component (e), component (g) is identified above as component (f), and component (h) is identified above as component (g).

(e) Electron Donor Photosensitizers Other than Pyrene

Useful electron donor photosensitizers should be soluble in the photocurable composition, free of functionalities that would substantially interfere with the cationic photocuring process, and capable of light absorption (sensitivity) within the range of wavelengths of at least 150 nm and up to and including 1000 nm.

Suitable electron donor photosensitizers initiate the chemical transformation of the onium salt (or other photoacid generator) in response to the photons absorbed from the irradiation. The electron donor photosensitizer should also be capable of reduce the photoacid generator after the electron donor photosensitizer has absorbed light (that is, photoinduced electron transfer). Thus, the electron donor photosensitizer, upon absorption of photons from irradiation, is generally capable of donating an electron to the photoacid generator.

For uses of the photocurable compositions in which very rapid curing (such as the curing of thin applied films of the compositions) is desired, the electron donor photosensitizers can have an extinction coefficient of at least 1000 liter-mole$^{-1}$ cm$^{-1}$ and typically at least 50,000 liters-mole$^{-1}$ cm$^{-1}$ at the desired irradiation wavelength using the photocuring process.

For example, each of the electron donor photosensitizers generally has an oxidation potential of at least 0.4 V and up to and including 3 V vs. SCE, or more typically of at least 0.8 V and up to and including 2 V vs. SCE.

In general, many different classes of compounds can be used as electron donor photosensitizers for various reactants. Useful electron donor photosensitizers include but are not limited to, aromatics such as naphthalene, 1-methylnaphthalene, anthracene, 9,10-dimethoxyanthracene, benz[a]anthracene, phenanthrene, benzo[c]phenanthrene, and fluoranthene. Pyrene is specifically excluded from these classes of component (e).

Other useful electron donor photosensitizers that involve the triplet excited state are carbonyl compounds such as thioxanthones and xanthones. Ketones including aromatic ketones such as fluorenone, and coumarin dyes such as keto-coumarins such as those with strong electron donating moieties (such as dialkylamino) can also be used as electron donor photosensitizers. Other suitable electron donor photosensitizers are believed to include xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriarylmethanes, merocyanines, squarylium dyes, and pyridinium dyes.

It is also possible to use a mixture of electron donor photosensitizers that are chosen from the same or different classes of materials.

Useful electron donor photosensitizers are available from various commercial sources and can be readily found for use in the present invention.

The one or more electron donor photosensitizers can be present in the photocurable composition in an amount of at least 0.0001 weight % and up to and including 5 weight %, and typically at least 0.001 weight % and up to and including 2 weight %, based on the total solids of the photocurable composition. Exact amounts of required electron donor photosensitizers depend on overall photocurable composition, application, and the extinction coefficient. Generally, if the extinction coefficient of the electron donor photosensitizer is high, which corresponds to higher light absorption efficiency, smaller amounts are required.

In some embodiments, the electron donor photosensitizer is a benzopyrene, perylene, or benzoperylene that is present in an amount of at least 0.05 weight % and up to and including 2 weight %, based on the total solids of the photocurable composition.

All of the photocurable compositions of Classes I through III can include various other components that are described as follows.

It is also possible include conductive nano-oxides and conductive nano-carbon materials such as nano-tubes, nano-graphene, and bucky balls. Conductive nano-oxides include but are not limited to, indium tin oxide, antimony oxide, antimony tin oxides, indium oxide, zinc oxide, zinc aluminum oxide, and mixtures thereof.

It can be useful to include one or more hydroxy-containing materials, including polyols, in the photocurable composition as charge transfer agents to aid in the photopolymerization process. The term "polyol" refers to an organic compound having two or more primary or secondary aliphatic hydroxy groups in the molecule. Each hydroxy (or hydroxyl) group in a hydroxy-containing material is directly bonded to a non-aromatic carbon atom in the molecule. When used, the hydroxy-containing materials can be in liquid or solid form and have an organic nature. Any of the hydroxyl groups can be terminally situated, or pendant from a homopolymer or copolymer backbone. The molecular weight of useful hydroxy-containing materials can be as low as 32 and up to one million or more for the polymeric polyols.

Useful hydroxy-containing materials can optionally contain other functionalities (besides the hydroxy groups) that do not substantially interfere with cationic photopolymerization at room temperature according to the present invention. Thus, the hydroxy-containing material can be either non-aromatic in nature or contain aromatic functionality, and can contain heteroatoms in the backbone of the molecule, including but not limited to, nitrogen, oxygen, and sulfur atoms, provided that such heteroatoms do not substantially interfere with cationic photopolymerization at room temperature according to the present invention. Useful polyols can be selected naturally occurring or synthetically prepared cellulosic materials.

The hydroxy-containing materials can be also substantially free of groups that can be thermally or photolytically unstable, that is, the hydroxy-containing materials will not decompose or liberate volatile components at temperatures below about 100° C. or in the presence of actinic light that is used during photopolymerization.

Representative examples of suitable hydroxy-containing materials having a single hydroxy group include but are not limited to, alkanols, monoalkyl ethers of polyoxyalkyleneglycols, monoalkyl ethers of alkylene-glycols, and other compounds that would be readily apparent to one skilled in the art.

The amount of hydroxy-containing material that can be present in the photocurable compositions can be up to and including 20 weight %, or particular at least 0.5 weight % and up to and including 5 weight % based on the total solids of the photocurable composition.

Addition of vinyl ether compounds as chain transfer agents to the photopolymerizable conductive compositions can also be desirable to further increase photopolymerization rates or ensure desired physical properties in the final photocured composition. Examples of useful vinyl ether compounds include but are not limited to, Rapi-Cure™ DVE-3 (triethyleneglycol divinylether), Rapi-Cure™ CHVE (1,4-cyclohexane dimethanoldivinylether), and Rapi-Cure™ HBVE (butanediol monovinylether), all available from Ashland Inc.). These vinyl ether compounds can be present in an amount of at least 0.1 weight % and up to and including 2 weight %, based on the total weight of the photocurable compositions.

The photocurable compositions can also contain suitable adjuvants (or additives) such as accelerators, inhibitors, absorbers, stabilizers, pigments, dyes, UV absorbers, viscosity modifiers, flow improvers, surface tension depressants and wetting aids, antioxidants, surfactants, and other ingredients well known to those skilled in the art. Silane coupling agents can be present to improve attachability of the metal nanoparticles to a substrate.

The amounts and types of essential and optional components in each photocurable composition can be readily adjusted to provide the desired physical and handling properties before and after photocuring (photopolymerization).

The photocurable compositions are generally prepared for coating, printing, or other means of application by simply admixing, under "safe light" conditions the various components. Such components can be mixed and dispersed within suitable organic solvents.

Pyrene Monitoring Methods

A photocurable or thermally curable composition can be provided in any suitable form. In most embodiments, a precursor article is formed to have a coating or pattern of photocurable or thermally curable composition can be used individually as a single element, or in alternative embodiments described below, a web (for example, a roll-to-roll continuous web) of multiple precursor articles in multiple portions of a continuous web of substrate can be exposed as the web is passed through exposure stations, or the exposure device is passed over the web. The same or different photocurable or thermally curable compositions can be provided in the precursor articles (for example, printed) on both supporting sides of a substrate whether it is in the form of a single element or continuous web. In many embodiments, different conductive metal patterns are formed on opposing supporting sides of the substrate (or continuous web) using the same or different photocurable or thermally curable composition.

For example, the photocurable or thermally curable composition can be provided as a uniform layer (coating) or in a pattern-wise manner to one or both supporting sides of any suitable substrate using any means for application, such as dip coating, roll coating, hopper coating, spray coating, spin coating, ink jetting, photolithographic imprinting, "flexographic" printing using printing elements including flexographic printing members (such as flexographic printing plates and flexographic printing sleeves), lithographic printing using lithographic printing plates, and gravure or intaglio printing using appropriate printing members.

The fluorescence monitoring process then requires the detection (or determining) of a first fluorescence emission spectrum emitted by the pyrene that is within the photocurable or thermally curable composition. This fluorescence emission spectrum typically has two or more peaks that can be evaluated for example using a standard fluorescence spectrophotometer that can be obtained from various commercial sources. For example one can measure or evaluate the peak intensity of two chosen peaks in the fluorescence emission spectrum, for example, recording or measuring the peak intensity of peak 1 to peak 3 in the multi-peak fluorescence emission spectrum.

After this evaluation of the first fluorescence emission spectrum, the photocurable or thermally curable composition, in whatever form it has been provided, is at least partially (in most embodiments essentially entirely or at least 95%) cured in a suitable manner. For example, thermal curing can be achieved by suitable heating process at a suitable temperature. Photocuring can be achieved by irradiation using appropriate exposing sources. For example, for many photocurable compositions useful in the practice of this invention, photocuring can be achieved using UV or visible irradiation having a wavelength of at least 184.5 nm to 600 nm and at intensity of at least 1 mJ/cm$^2$ and up to and including 1000 mJ/cm$^2$, or more typically of at least 1 mJ/cm$^2$ and up to and including 800 mJ/cm$^2$. One or more suitable light sources can be used for the exposure process as would be readily apparent to one skilled in the art.

When the photocurable or thermally curable composition is uniformly applied to a supporting side of a suitable substrate, it can be "imaged" or selectively exposed (or patterned) with curing means such as exposing radiation through a suitable photomask (masking element) having the desired pattern, or patterned heating, and then appropriately removing the non-crosslinked photocurable or thermally curable composition using a suitable "developer" solution. These features or steps can be carried out on a single or both (opposing) supporting sides of the substrate.

Suitable substrates (also known as "receiver elements") can be composed of any suitable material as long as it does not inhibit the purpose of the photocurable or thermally curable composition. For example, substrates can be formed from materials including but not limited to, polymeric films, metals, glasses (untreated or treated for example with tetrafluorocarbon plasma, hydrophobic fluorine, or a siloxane water-repellant material), silicon or ceramic wafers, fabrics, papers, and combinations thereof (such as laminates of various films, or laminates of papers and films) provided that a uniform layer or pattern of a photocurable or thermally curable composition can be formed thereon in a suitable manner and followed by irradiation to form a uniform cured layer or cured pattern on at least one receptive surface (supporting side) thereof. The substrate can be transparent or opaque, and rigid or flexible. The substrate can include one or more auxiliary polymeric or non-polymeric layers or one or more patterns of other materials before a pattern of photocurable or thermally curable composition is applied.

A supporting side of the substrate can be treated for example with a primer layer or electrical or mechanical treatments (such as graining) to render that surface a "receptive surface" to improve adhesion of the photocurable or thermally curable composition and resulting cured layer or pattern, or of a separate adhesive layer. An adhesive layer can be disposed on the substrate and this adhesive layer can have various properties in response to stimuli (for example, it can be thermally activated, solvent activate, or chemically activated) and that serves as a receptive layer. Useful adhesive materials of this type are described for example in [0057] of U.S. Patent Application 2008/0233280 (Blanchet et al.).

In some embodiments, the substrate comprises a separate receptive layer as a receptive surface disposed on a substrate, which receptive layer and substrate can be composed of a material such as a suitable polymeric material that is highly receptive of the photocurable or thermally curable composition. Such receptive layer can have a dry thickness of at least 0.05 µm and up to and including 10 µm, or typically of at least 0.05 µm and up to and including 3 µm, when measured at 25° C.

A supporting side (or surface) of the substrate, especially polymeric substrates, can be treated by exposure to corona discharge, mechanical abrasion, flame treatments, or oxygen plasmas, or by coating with various polymeric films, such as poly(vinylidene chloride) or an aromatic polysiloxane as described for example in U.S. Pat. No. 5,492,730 (Balaba et al.) and U.S. Pat. No. 5,527,562 (Balaba et al.) and U.S. Patent Application Publication 2009/0076217 (Gommans et al.).

Suitable substrate materials for forming articles include but are not limited to, metallic films or foils, metallic films on polymer, glass, or ceramic supports, metallic films on electrically conductive film supports, semi-conducting organic or inorganic films, organic or inorganic dielectric films, or laminates of two or more layers of such materials. For example, useful substrates can include polymeric films such as poly (ethylene terephthalate) films, poly(ethylene naphthalate) films, polyimide films, polycarbonate films, polyacrylate films, polystyrene films, polyolefin films, and polyamide films, silicon and other ceramics, metal foils such as aluminum foils, cellulosic papers or resin-coated or glass-coated papers, glass or glass-containing composites, metals such as aluminum, tin, and copper, and metalized films. The substrate can also include one or more charge injection layers, charge transporting layers, and semi-conducting layers on which the photocurable or thermally curable composition pattern is formed.

Particularly useful substrates are polyesters films such as poly(ethylene terephthalate), poly(ethylene naphthalate), polycarbonate, or poly(vinylidene chloride) films with or without surface-treatments as noted above, or coatings.

Useful substrates can have a desired dry thickness depending upon the eventual use of the article formed therefrom, for example its incorporation into various articles or optical or display devices. For example, the substrate dry thickness (including all treatments and auxiliary layers) can be at least 0.001 mm and up to and including 10 mm, and especially for polymeric films, the substrate dry thickness can be at least 0.008 mm and up to and including 0.2 mm.

The substrate used to prepare the articles can be provided in various forms, such as for example, individual sheets in any size or shape, and continuous webs such as continuous webs of transparent substrates including transparent polyester substrates that are suitable for roll-to-roll operations. Such continuous webs can be divided or formed into individual first, second, and additional portions that can be used to form the same or different photocured or thermally cured patterns from the same or different photocurable or thermally cured compositions.

A photocurable or thermally curable composition can be subjected to an ultrasonication process if desired to increase the dispersibility of the various components and especially the metal particles. After application, any inert organic solvents can be removed by drying or pre-baking procedure that does not adversely affect the remaining components or prematurely cause polymerization. Useful drying conditions can be as low as room temperature for as little as 5 seconds and up to and including several hours depending upon the manufacturing process. In most processes, such as roll-to-roll processes described below, the drying conditions can be at high enough temperatures to remove at least 90% of the inert organic solvent within at least 1 second.

Any applied layer of the photocurable or thermally curable composition can have a dry thickness of at least 0.1 µm and up to and including 10 µm, or typically at least 0.2 µm and up to and including 5 µm, and the optimal dry thickness can be tailored for the intended use of the resulting cured layer, which generally has about the same dry thickness as the layer of the non-cured photocurable or thermally curable composition. Such a layer can be applied to both (opposing) supporting sides of the substrate, which layers can have the same or different chemical compositions or dry thickness and can be uniform in dry thickness and composition.

Any applied pattern of the photocurable or thermally curable composition can comprise a grid of lines (or other shapes including circles or an irregular network) having an average thickness (or width) of at least 1 µm and up to and including 20 µm, or typically of at least 1 µm and up to and including 10 µm, and the optimal dry thickness (or width) can be tailored for the intended use of the resulting uniform cured layer, which generally has about the same dry thickness (or width) as the grid lines of the non-cured photocurable or thermally curable composition.

At some point after curing is begun (for example when at least 10% of the one or more photocurable or thermally curable components can be cured), a second fluorescence emission spectrum emitted by pyrene in the at least partially cured composition is obtained and evaluated. The first fluorescence emission spectrum emitted by the pyrene is then compared in a suitable manner to the second fluorescence emission spectrum. For example, the heights of the same two predetermined separate emission peaks in each fluorescence emission spectrum are compared and the change in the difference in heights between these two predetermined selected peaks is indicative of the extent of curing. Thus, one skilled in the art could decide to compare emission peaks 1 and 3 (for example, these peaks are more sensitive to polarity changes) in each of the pyrene fluorescence emission spectrums that are evaluated.

This comparing process can be carried out multiple times during a particular process or manufacturing operation for example to evaluate the extent of curing and its progress throughout the entire operation. This continuous evaluation merely requires that the second and additional fluorescence emission spectra obtained as desired intervals are individually compared to the first fluorescence emission spectrum, or even compared to any preceding fluorescence emission spectrum.

The present invention can be carried out using articles comprising a substrate and uniform layers or patterns of the photocurable or thermally curable composition, wherein such articles can be considered "precursor" articles, meaning that they are the first articles produced in methods used to provide conductive articles.

In some embodiments, the same or different photocurable or thermally curable composition can be applied in a suitable manner on both supporting sides (main surfaces) of the substrate to form "duplex" or dual-sided precursor articles, and each applied composition can be in the form of the same or different uniform layer or pattern.

In many embodiments, a pattern of the photocurable or thermally curable composition is applied on one or both (opposing) supporting sides of the substrate (for example as a roll-to-roll web) using a relief element such as elastomeric relief elements derived from flexographic printing plate precursors, many of which are known in the art and some are commercially available, for example as the Cyrel® Flexographic Photopolymer Plates from DuPont and the Flexcel™ SR and NX Flexographic plates from Eastman Kodak Company.

Particularly useful elastomeric relief elements are derived from flexographic printing plate precursors and flexographic printing sleeve precursors, each of which can be appropriately imaged (and processed if needed) to provide the relief elements for "printing" or applying a suitable pattern.

In other embodiments, the elastomeric relief element is provided from a direct (or ablation) laser-engraveable elastomer relief element precursor, with or without integral masks, as described for example in U.S. Pat. No. 5,719,009 (Fan), U.S. Pat. No. 5,798,202 (Cushner et al.), U.S. Pat. No. 5,804,353 (Cushner et al.), U.S. Pat. No. 6,090,529 (Gelbart), U.S. Pat. No. 6,159,659 (Gelbart), U.S. Pat. No. 6,511,784 (Hiller et al.), U.S. Pat. No. 7,811,744 (Figov), U.S. Pat. No. 7,947,426 (Figov et al.), U.S. Pat. No. 8,114,572 (Landry-Coltrain et al.), U.S. Pat. No. 8,153,347 (Veres et al.), U.S. Pat. No. 8,187,793 (Regan et al.), and U.S. Patent Application Publications 2002/0136969 (Hiller et al.), 2003/0129530 (Leinenback et al.), 2003/0136285 (Telser et al.), 2003/0180636 (Kanga et al.), and 2012/0240802 (Landry-Coltrain et al.).

Once provided on the substrate, and the first fluorescence emission has been determined, either in a uniform layer or predetermined pattern of grid lines or other shapes (on one or opposing sides of the substrate), the photocurable or thermally curable composition in the precursor article can be cured (for example, irradiated with suitable radiation as described above from a suitable source such as a fluorescent lamp or LED) to provide a cured layer or cured pattern on the substrate. For example, photocuring can be achieved by the use of UV-visible irradiation having a wavelength ($\lambda_{max}$) of at least 190 nm and up to and including 700 nm and at intensity of at least 1,000 microwatts/cm$^2$ and up to and including 80,000 microwatts/cm$^2$. The irradiation system used to generate such radiation can consist of one or more ultraviolet lamps for example in the form of 1 to 50 discharge lamps, for example, xenon, metallic halide, metallic arc (such as a low, medium or high pressure mercury vapor discharge lamps having the desired operating pressure from a few millimeters to about 10 atmospheres). The lamps can include envelopes capable of transmitting light of a wavelength of at least 190 nm and up to and including 700 nm or typically at least 240 nm and up to and including 450 nm. Typical lamps that can be employed for providing ultraviolet radiation are, for example, medium pressure mercury arcs, such as the GE H3T7 arc and a Hanovia 450 W arc lamp. Photocuring can be carried out using a combination of various lamps, some of or all of which can operate in an inert atmosphere. When using UV lamps, the irradiation flux impinging upon the substrate (or applied layer or pattern) can be at least 0.01 watts/inch$^2$ (0.0197 watts/cm$^2$) to effect sufficient rapid photopolymerization and photocuring of the applied photocurable composition within 1 to 20 seconds in a continuous manner, for example in a roll-to-roll operation.

An LED irradiation device to be used in the photocuring process can have an emission peak wavelength of 350 nm or more. The LED device can include two or more types of elements having different emission peak wavelengths greater than or equal to 350 nm. A commercial example of an LED device that has an emission peak wavelength of 350 nm or more and has an ultraviolet light-emitting diode (UV-LED), is NCCU-033 that is available from Nichia Corporation.

The result of such curing, for example irradiation of a precursor article is an intermediate article comprising the substrate (for example, individual sheets or a continuous web) and having thereon either a cured layer or a cured pattern (containing suitable particles) on one or both supporting sides of the substrate, each of which is derived from a photocurable or thermally curable composition as described above comprising pyrene.

At one or more times during or after the curing operation, a second or additional fluorescence emission spectra emitted by the pyrene in the resulting at least partially cured composition (in each cured pattern) is determined using the same procedures described above for determining the first fluorescence. As noted above, the second or additional fluorescence emission spectra can be compared, for example, by evaluating and comparing the changes in specific spectral peaks.

This procedure of determining and comparison multiple fluorescence spectra emitted by the pyrene in the photocurable or thermally curable and at least partially cured compositions can be carried out on either or both supporting sides of the substrate. For example, multiple fluorescence emission spectra can be determined and compared for one supporting side of a transparent polymeric substrate, and multiple fluorescence emission spectra can be determined and compared for the opposing second supporting side of a transparent polymeric substrate. Multiple fluorescence emission spectra can be determined and compared for each cured portion (or pattern) that is prepared in a given article or continuous web.

The resulting intermediate articles can be used in this form for some applications, but in most embodiments, they are further processed to incorporate an electrically conductive metal on the uniform cured layer or cured pattern, each of which includes metal particles that act as "seed" materials for further application of electrically conductive metals, for example by using electroless metal procedures. For example, the electroless "seed" metal particles are described above as component (e) but particularly useful metal particles include gold, silver, palladium, copper, and platinum particles that can be electrolessly plated with silver, copper, platinum, palladium, nickel, or other metals described below.

One useful method uses multiple flexographic printing plates (for example, prepared as described above) in a stack in a printing station wherein each stack has its own printing plate cylinder so that each flexographic printing plate is used to print individual substrates, or the stack of printing plates can be used to print multiple portions in a substrate web (on one or both supporting sides). The same or different photocurable or thermally curable composition can be "printed" or applied to a substrate (on same or both supporting sides) using the multiple flexographic printing plates.

In other embodiments, a central impression cylinder can be used with a single impression cylinder mounted on a printing press frame. As the substrate (or receiver element) enters the printing press frame, it is brought into contact with the impression cylinder and the appropriate pattern is printed with the photocurable composition. Alternatively, an in-line flexographic printing process can be utilized in which the printing stations are arranged in a horizontal line and are driven by a common line shaft. The printing stations can be coupled to exposure stations, cutting stations, folders, and other post-processing equipment. A skilled worker could readily determine other useful configurations of equipment and stations using information that is available in the art. For example, an in-the-round imaging process is described in WO 2013/063084 (Jin et al.).

This intermediate article can be immediately immersed in an aqueous-based electroless metal plating bath or solution, or the intermediate article can be stored with just the catalytic pattern comprising corresponding electroless seed metal particles (such as the metal particles described above) for use at a later time.

The intermediate article can be contacted with an electroless plating metal that is the same as or different from the corresponding electroless seed metal particles. In most embodiments, the electroless plating metal is a different metal from the corresponding electroless seed metal particles.

Any metal that will likely electrolessly "plate" on the corresponding electroless seed metal particles can be used at this point, but in most embodiments, the electroless plating metal can be for example copper(II), silver(I), gold(IV), palladium (II), platinum(II), nickel(II), chromium(II), and combinations thereof. Copper(II), silver(I), and nickel(II) are particularly useful electroless plating metals.

The one or more electroless plating metals can be present in an aqueous-based electroless plating bath or solution in an amount of at least 0.01 weight % and up to and including 20 weight % based on total electroless plating solution weight.

Electroless plating can be carried out using known temperature and time conditions, as such conditions are well known in various textbooks and scientific literature. It is also known to include various additives such as metal complexing agents or stabilizing agents in the aqueous-based electroless plating solutions. Variations in time and temperature can be used to change the metal electroless plating thickness or the metal electroless plating deposition rate.

A useful aqueous-based electroless plating solution or bath is an electroless copper(II) plating bath that contains formaldehyde as a reducing agent. Ethylenediaminetetraacetic acid (EDTA) or salts thereof can be present as a copper complexing agent. Other useful aqueous-based electroless plating solutions or baths comprise silver(I) with EDTA and sodium tartrate, silver(I) with ammonia and glucose, copper(II) with EDTA and dimethylamineborane, copper(II) with citrate and hypophosphite, nickel(II) with lactic acid, acetic acid, and a hypophosphite, and other industry standard aqueous-based electroless baths or solutions such as those described by Mallory et al. in *Electroless Plating: Fundamentals and Applications* 1990.

After the electroless plating procedure to provide a conductive metal pattern on one or more portions of one or both supporting sides of the substrate, the resulting product article can be removed from the aqueous-based electroless plating bath or solution and can again be washed using distilled water or deionized water or another aqueous-based solution to remove any residual electroless plating chemistry.

In some embodiments, the resulting product article can be rinsed or cleaned with water at room temperature as described for example in [0048] of WO 2013/063183 (Petcavich), or with deionized water at a temperature of less than 70° C. as described in [0027] of WO 2013/169345 (Ramakrishnan et al.).

To change the surface of the electroless plated metal for visual or durability reasons, it is possible that a variety of post-treatments can be employed including surface plating of still at least another (third or more) metal such as nickel or silver on the electrolessly plated metal (this procedure is sometimes known as "capping"), or the creation of a metal oxide, metal sulfide, or a metal selenide layer that is adequate to change the surface color and scattering properties without reducing the conductivity of the electrolessly plated (second) metal. Depending upon the metals used in the various capping procedures of the method, it may be desirable to treat the electrolessly plated metal with a suitable seed metal catalyst in an aqueous-based seed metal catalyst solution to facilitate deposition of additional metals.

Thus, in some embodiments of the method for providing a product article, the method comprises:

(i) providing a continuous web of a transparent substrate of any of those materials described above, but particularly transparent polymeric substrates, (ii) forming a photocurable or thermally curable pattern on at least a first portion of a supporting side of the continuous web using a photocurable or thermally curable composition as described above comprising pyrene, for example using a flexographic printing member, (ii') determining a first fluorescence emission spectrum emitted by the pyrene in the photocurable or thermally curable composition, (iii) curing the photocurable or thermally curable pattern to form a cured pattern comprising pyrene on the first portion, (iii') determining a second fluorescence emission spectrum emitted by the pyrene in the cured pattern, (iii") comparing the first fluorescence emission spectrum and the second fluorescence emission spectrum to determine an extent of curing in the cured pattern, and (iv) electrolessly plating the cured pattern on the first portion with an electrically conductive metal, using electroless plating procedures described above.

Embodiments of this method can be carried out on a single supporting side of the substrate, or on opposing supporting sides of the substrate to provide the same or different patterns of electrically conductive metals. In all embodiments, the pyrene monitoring process can be used to determine the extent of curing in any or all of the patterns.

The apparatus for measuring fluorescence includes a source of excitation energy, an analytical head which will preferably access multiple sites on a coated substrate of any size and shape, a detector for measuring the emitted radiation, and data processing software so that the monitored polymer property may be determined at any point along the substrate by comparison to calibration data. Any fluorescence of measurable intensity is useful. The apparatus can be designed to detect selected wavelengths in the emission spectrum or to detect the entire spectrum.

Any convenient source of energy that will activate the fluorescence emission of pyrene probe can be employed and any means capable of detecting the fluorescence emission can be used in the present invention. Suitable examples of excitation sources include ultraviolet radiation from a xenon or mercury lamp, or lasers. The apparatus can employ a bifurcated optical fiber array wherein one set of fibers provides the excitation energy to the substrate or coating and another associated set of fibers is coupled to a photodetector and detects fluorescence. This array can assume any design configuration necessary to accommodate the substrate being coated. However, the array will likely be housed in a light-tight chamber. In one embodiment a linear array of optical fiber pairs (that is, one fiber for excitation and the other for detection) can be positioned immediately adjacent to the coated substrate for monitoring in the production environment.

The apparatus can include other components of a conventional fluorimeter such as an electronic shutter, a monochromator, a photomultiplier tube, a photodiode array or CCD as the radiation detector, analog to digital converters that interface with the detector, focusing lenses, interference filters, or neutral density filters.

As would be apparent to one skilled in the art, a plurality of portions having the same or different cured patterns can be provided on this continuous web (on one or both opposing supporting sides).

For example, a method for providing a plurality of product articles comprises:

(i) providing a continuous web of a transparent substrate, (ii) forming a photocurable or thermally curable pattern on at least a first portion of at least one supporting side of the continuous web using a photocurable or thermally curable composition as described above that comprises pyrene, (ii') determining a first fluorescence emission spectrum emitted by the pyrene in the photocurable or thermally curable composition, (iii) curing the photocurable or thermally curable pattern to form a cured pattern on the first portion, (iii') determining a second fluorescence emission spectrum emitted by pyrene in the cured pattern, (iii") comparing the first fluorescence emission spectrum and the second fluorescence emission spectrum to determine an extent of curing in the cured pattern, (iv) electrolessly plating the cured pattern on the first portion with an electrically conductive metal (as described above), and (v) repeating features (ii) through (iv) on one or more additional portions of the continuous web that are different from the first portion, using the same or different photocurable or thermally curable composition.

This method can be used to similarly form electrically conductive metal patterns on the opposing (second) supporting side of the substrate, especially when the substrate is a continuous web of material such as a polymeric web.

Alternatively, a method of this invention can be used to provide a plurality of precursor articles, the method comprising:

(i) providing a continuous web of a transparent substrate (such as a continuous web of a transparent polymer) as described above, (ii) forming a first photocurable or thermally curable pattern on a first portion of at least one supporting side of the continuous web by applying a photocurable or thermally curable composition comprising pyrene to the first portion using a flexographic printing member as described above, (ii') determining a first fluorescence emission spectrum emitted by the pyrene in the first portion, (iii) advancing the continuous web comprising the first portion comprising the first photocurable or thermally curable pattern to be proximate exposing radiation, and thereby forming a first cured pattern on the first portion, (iv) forming a second photocurable or thermally curable pattern on a second portion of the continuous web by applying the same or different photocurable or thermally curable composition comprising pyrene to the second portion using the same or different flexographic printing member, (iv') determining a first fluorescence emission spectrum emitted by the pyrene in the second portion, (v) advancing the continuous web comprising the second portion comprising the second photocurable or thermally curable pattern to be proximate exposing radiation, and thereby forming a second cured pattern on the second portion, (vi) optionally, carrying out features (iv), (iv'), and (v') one or more times on additional respective portions of the continuous web using the same or different photocurable or thermally curable composition comprising pyrene, and the same or different flexographic printing member to form additional cured patterns on the additional respective portions, (vi') determining a second fluorescence emission spectrum emitted by the pyrene is any of the first portion, second portion, and any additional respective portions, (vi") comparing each first fluorescence emission spectrum and any respective second fluorescence emission spectrum to determine an extent of curing in any of the first portion, second portion, and additional respective portions, and (vii) winding up the continuous web comprising multiple cured patterns.

As would be apparent from other teaching in this disclosure, such method embodiments can be carried out on opposing supporting sides of the continuous web to provide same or different multiple cured patterns on those opposing sides.

In still other embodiments, a method of this invention can be used to provide a plurality of electrically conductive metal patterns, comprises:

providing a continuous web comprising multiple cured patterns in respective portions, each cured pattern being provided by curing a photocurable or thermally curable composition as described above, treating the continuous web comprising multiple cured patterns with an electroless metal plating solution to provide multiple electrolessly plated metal patterns on the continuous web in the respective portions, and optionally, further treating the multiple electrolessly plated metal patterns with a capping metal to provide multiple capped electrically conductive patterns on the continuous web. During this method, the multiple fluorescence emission spectra can be determined and compared as described above to determine the extent of curing in any or all of the electrolessly plated metal patterns.

This method can be taken further by:

forming individual electrically conductive articles from the continuous web comprising multiple capped electrically conductive patterns, and assembling the individual electrically conductive articles into the same or different individual devices.

Such method embodiments can be carried out on both supporting sides of the substrates using the same or different photocurable or thermally curable compositions comprising pyrene.

Useful product articles prepared according to the present invention can be formulated into capacitive touch screen sensors that comprise suitable electrically conductive grid lines, electrodes, electrical leads, and electrical connectors. For example, the electrodes and tail can be formed by printing the photocurable or thermally curable composition and electrolessly plating the printed patterns. The electrodes can form an x-y grid that enables the recognition of the point at which the user has interacted with the sensor. For example, the grid can have 16×9 conductive lines or more and a size range of for example, from 2.5 mm by 2.5 mm to 2.1 m by 2.1 m. Top electrodes in the product article can correspond to the Y axis and were provided on a first side of the substrate and bottom electrodes are electrically conductive lines corresponding to the X axis provided on the opposing side of the substrate.

Some details of useful methods and apparatus for carrying out the method are described for example in WO 2013/063183 (Petcavich), WO 2013/169345 (Ramakrishnan et al.). Other details of a useful manufacturing system for preparing electrically conductive articles especially in a roll-to-roll manner are provided in PCT/US/062366, filed Oct. 29, 2012 by Petcavich and Jin, the disclosure of which is incorporated herein by reference.

An additional system of equipment and step features that can be used in carrying out the present invention is described in U.S. Ser. No. 14/146,867 filed Jan. 3, 2014 by Shifley, which is incorporated herein by reference for all details that are pertinent to methods of the present invention.

Pyrene also can be used to monitor or determine the loss of organic solvents in a solution, dispersion, or composition containing such one or more inert organic solvents. This is possible because the fluorescence emission spectrum emitted by pyrene readily changes when the polarity of its environment (such as the solution, dispersion, or composition) changes. A sufficient loss in the amount of inert organic solvents changes that polarity so that the difference in fluorescence emission spectrum emitted by pyrene can be observed and determined. This change in fluorescence emission spectrum can be determine in the same manner as described above for the detection of the extent of curing. That is, a change in predetermined peaks in the fluorescence emission spectra taken at various times can be compared and evaluated.

For example, when photocurable or thermally curable compositions containing at least one photocurable or thermally curable component are prepared for use, inert organic solvents used in such compositions can evaporate or be otherwise lost before or during use of the compositions. Pyrene can be added to such composition and one can obtain a fluorescence emission spectrum emitted by pyrene at the time the photocurable or thermally curable composition is prepared, and then measure the fluorescence emission spectrum emitted by pyrene one or more times later on to determine if any inert organic solvent has evaporated or been removed in any other manner such as during coating or printing operations. Thus, one can compare two or more predetermined emission peaks in the fluorescence emission spectra to see how they have changed. This information can tell the operator if more inert organic solvent(s) should be added or if other components in the photocurable or thermally curable composition should be adjusted (added or diluted) during a manufacturing operation, for example during "printing" or coating the photocurable to thermally curable composition onto a substrate.

The loss in inert organic solvent(s) carried out using this method is not necessarily dependent upon the particular solvents, but it would be apparent to one skilled in the art that more volatile inert organic solvents could be more readily "lost" and the monitoring method described herein could be more critical for maintaining high quality in a manufacturing operation, such as a printing or coating operation, in such cases. Inert organic solvents that could be present include any of those described above for the photocurable or thermally curable compositions.

After the detection of any loss in inert organic solvent(s), one skilled in the art can readily replenish the lost amounts if necessary to maintain quality operations or curing reactions.

It is further possible to use pyrene as a fluorescence monitor to detect any premature (unwanted) reaction before a photocurable or thermally curable composition is used and curing is purposely initiated. As noted above, such photocurable or thermally curable compositions need only comprise at least one photocurable or thermally curable component that would be readily known to one skilled in the art, and especially in view of the teaching above regarding specific photocurable and thermally curable components.

Thus, a photocurable or thermally curable composition to be evaluated is provided with pyrene and a first fluorescence emission spectrum emitted by the pyrene is determine as described above. After an elapsed time, which could be predetermined or not, a second fluorescence emission spectrum emitted by the pyrene is determined and the two fluorescence emission spectra are compared as described above to determine if any premature curing or other reaction has occurred. With this information, the operator can decide to continue use of the photocurable or thermally curable composition or to discard it if premature reaction or curing is too extensive.

Another use for fluorescence emission spectra emitted by pyrene is to determine the extent of photocuring in a dried layer of a thermally-curable or photocurable composition. This can be done by providing a dried layer of a thermally-curable or photocurable composition comprising at least one thermally-curable or photocurable component (representative thermally curable and photocurable components and compositions are described above) and pyrene that is disposed over a supporting side of a transparent polymeric substrate. Thus, the dried thermally-curable or photocurable layer can be directly disposed on the transparent substrate, or there can be one or more intermediate layers as long as they are sufficient transparent so that the fluorescence emission spectrum emitted by the pyrene can be readily detected.

The dried layer has both an outermost surface (farther from the transparent substrate) and an innermost surface (closer to the transparent substrate) that are separated by an average dry thickness so that there is a dry thickness profile from one surface to the other surface of the dried layer. The average dry thickness can be in useful dimension but typically it is at least 0.1 μm and up to and including 10,000 μm.

The thermally-curable or photocurable composition can then be exposed in a suitable manner as described above to provide an at least partially thermally cured or photocured composition or at least partially thermally cured or photocured dried layer having the corresponding innermost surface and outermost surface.

A first fluorescence emission spectrum emitted by the pyrene at the innermost surface of the at least partially thermally cured or photocured dried layer is determined, as well s a second fluorescence emission spectrum emitted by the pyrene at the outermost surface of the at least partially thermally cured or photocured dried layer.

The dried layer has both an outermost surface (farther from the transparent substrate) and an innermost surface (closer to the transparent substrate) that are separated by an average dry thickness so that there is a dry thickness profile from one surface to the other surface of the dried layer. The average dry thickness can be in useful dimension but typically it is at least 0.1 μm and up to and including 10,000 μm.

The thermally-curable or photocurable composition can then be exposed in a suitable manner as described above to provide an at least partially thermally cured or photocured composition or at least partially thermally cured or photocured dried layer having the corresponding innermost surface and outermost surface.

A first fluorescence emission spectrum emitted by the pyrene at the innermost surface of the at least partially thermally cured or photocured dried layer is determined, as well s a second fluorescence emission spectrum emitted by the pyrene at the outermost surface of the at least partially thermally cured or photocured dried layer.

This is usually accomplished by recording fluorescence emission spectrum in front-face fluorescence detection mode which is ideal for solid, turbid, or highly absorbent samples such as pellets, powders, and monolayers on microscope slides. In front-face viewing, the fluorescence is collected from the surface of sample and after this recording one could flip the sample and record emission from opposing surface.

Once these fluorescence emission spectra are obtained, they can be compared to determine any difference in thermally curing or photocuring between the outermost surface and the innermost surface of the at least partially thermally cured photocured dried layer. This difference can be determined as described above, for example by comparing the same predetermined peaks in the emission spectra.

The present invention provides at least the following embodiments and combinations thereof, but other combinations of features are considered to be within the present invention as a skilled artisan would appreciate from the teaching of this disclosure:

1. A method for determining the extent of curing in a layer of a photocurable or thermally curable composition, the method comprising:

providing a dried layer of a photocurable or thermally curable composition over a supporting side of a transparent polymeric substrate, the dried layer having an outermost surface and an innermost surface, and the photocurable or thermally curable composition comprising a photocurable or thermally curable component and pyrene, exposing the photocurable or thermally curable composition to form an at least partially photocured or thermally cured composition in an at least partially photocured or thermally cured dried layer having an innermost surface and an outermost surface, determining a first fluorescence emission spectrum emitted by the pyrene at the innermost surface of the at least partially photocured or thermally cured dried layer, determining a second fluorescence emission spectrum emitted by the pyrene at the outermost surface of the at least partially photocured or thermally cured dried layer, comparing the first fluorescence emission spectrum and the second fluorescence emission spectrum to determine any difference in curing between the outermost surface and the innermost surface of the at least partially photocured or thermally cured dried layer.

2. The method of embodiment 1, comprising providing the photocurable or thermally curable composition on a supporting side of a transparent polymeric substrate in a patternwise manner, the transparent polymeric substrate also comprising an opposing second supporting side.

3. The method of embodiment 2, comprising determining the first fluorescent emission spectrum and the second fluorescence emission spectrum from the opposing second supporting side of the transparent polymeric substrate.

4. The method of embodiment 2 or 3 comprising providing the photocurable or thermally curable composition as multiple patterns on the supporting side of the transparent polymeric substrate that is a transparent polymeric web.

5. The method of any of embodiments 2 to 4 comprising providing the photocurable or thermally curable composition as multiple patterns on the supporting side of the transparent polymeric substrate in a roll-to-roll fashion.

6. The method of any of embodiments 1 to 5, wherein the photocurable component is a photopolymerizable epoxy material.

7. The method of any of embodiments 1 to 6, wherein the exposing is sufficient to photocure at least 10 weight % of the photocurable component.

8. The method of any of embodiments 1 to 7, wherein the photocurable or thermally curable composition further comprises metal particles that have a particle size of at least 0.01 μm and up to and including 25 μm.

9. The method of any of embodiments 1 to 8, wherein the photocurable or thermally curable composition further comprises metal particles that are carbon-coated silver particles or carbon-coated copper particles.

10. The method of any of embodiments 1 to 6, wherein the photocurable composition further comprises a photoacid generator that is an iodonium or sulfonium salt.

11. The method of any of embodiments 1 to 10, wherein the pyrene is present in the photocurable or thermally curable composition in an amount of at least 0.0001 weight % and up to and including 10 weight % based on the total solids in the photocurable or thermally curable composition.

12. The method of any of embodiments 1 to 11, wherein the photocurable composition comprises one or more free radically polymerizable compounds as the photocurable component, and further comprises one or more free radical photoinitiators.

13. The method of any of embodiments 1 to 12, wherein comparing the first fluorescence emission spectrum and the second fluorescence emission spectrum is carried out by comparing first and second predetermined emission peaks in the first fluorescence emission spectrum and the second fluorescence emission spectrum.

14. The method of any of embodiments 1 to 13, wherein the dried layer has an average dry thickness of at least 0.1 μm and up to and including 10,000 μm.

Other useful embodiments are the following:

1. A method for determining loss of an organic solvent, the method comprising:

providing a photocurable or thermally curable composition comprising at least one photocurable or thermally curable components, one or more organic solvents, and pyrene, determining a first fluorescence emission spectrum emitted by the pyrene in the photocurable or thermally curable composition, after an elapsed time, determining a second fluorescence emission spectrum emitted by the pyrene in the photocurable or thermally curable composition, comparing the first fluorescence emission spectrum and the second fluorescence emission spectrum to determine an extent of loss of one or more organic solvents from the photocurable or thermally curable composition.

2. The method of embodiment 1, wherein the photocurable or thermally curable composition is a photocurable composition comprising at least one photocurable component.

3. The method of embodiment 1 or 2, wherein the composition is a photocurable composition, and the method comprises comparing the first fluorescence emission spectrum and the second fluorescence emission spectrum to determine an extent of loss of one or more organic solvents from the photocurable composition, the photocurable composition comprising:

(a) a photopolymerizable epoxy material,
(b) a photoacid generator,
(c) pyrene,
(d) one or more inert organic solvents,
(e) metal particles,
(f) optionally, a free radically polymerizable compound, and
(g) optionally, a free radical generating photoinitiator.

4. The method of any of embodiments 1 to 3, wherein the composition is a photocurable composition, and the method comprising comparing the first fluorescence emission spectrum and the second fluorescence emission spectrum to determine an extent of loss of one or more organic solvents from the photocurable composition, the photocurable composition comprising:

(a) a photopolymerizable epoxy material,
(b) a photoacid generator,
(c) pyrene,
(d) one or more inert organic solvents, (e) an electron acceptor photosensitizer,
(f) an electron donor co-initiator having an oxidation potential of 0.1 V to 3 V vs. SCE,
(g) metal particles,
(h) optionally, a free radically polymerizable compound, and
(i) optionally, a free radical generating photoinitiator.

5. The method of any of embodiments 1 to 4, wherein the composition is a photocurable composition, and the method comprising comparing the first fluorescence emission spectrum and the second fluorescence emission spectrum to determine an extent of loss of one or more organic solvents from the photocurable composition, the photocurable composition comprising:
(a) a photopolymerizable epoxy material,
(b) a photoacid generator,
(c) pyrene
(d) one or more inert organic solvents,
(e) an electron donor photosensitizer other than pyrene, which electron donor photosensitizer has an oxidation potential of at least 0.4 V and up to and including 3 V vs. SCE,
(f) metal particles,
(g) optionally, a free-radically polymerizable compound, and
(h) optionally, a free radical generating photoinitiator.

6. The method of embodiment 1, wherein the photocurable or thermally composition is a thermally curable composition.

7. The method of any of embodiments 1 to 6, wherein comparing the first fluorescence emission spectrum and the second fluorescence emission spectrum is carried out by comparing first and second predetermined emission peaks in the first fluorescence emission spectrum and the second fluorescence emission spectrum.

8. The method of any of embodiments 1 to 7, wherein after the comparing of the first and second fluorescence emission spectra, further comprising:
replenishing the one or more organic solvent(s) based on any detected loss.

Other embodiments are represented as follows:

1. A method for determining premature reaction before curing a photocurable or thermally curable composition, the method comprising:
providing a photocurable or thermally curable composition comprising a photocurable or thermally curable component and pyrene,
determining a first fluorescence emission spectrum emitted by the pyrene in the photocurable or thermally curable composition,
after an elapsed time, determining a second fluorescence emission spectrum emitted by the pyrene in the photocurable or thermally curable composition,
comparing the first fluorescence emission spectrum and the second fluorescence emission spectrum to determine an extent of curing in the photocurable or thermally curable composition.

2. The method of embodiment 1 comprising:
providing the photocurable or thermally curable composition on a supporting side of a transparent polymeric substrate in a patternwise manner, the transparent polymeric substrate also comprising an opposing second supporting side.

3. The method of embodiment 2, comprising:
determining the first fluorescent emission spectrum and the second fluorescence emission spectrum from the opposing second supporting side of the transparent polymeric substrate.

4. The method of embodiment 2 comprising:
providing the photocurable or thermally curable composition as multiple patterns on the supporting side of the transparent polymeric substrate that is a transparent polymeric web.

5. The method of embodiment 2 comprising providing the photocurable or thermally curable composition as multiple patterns on the supporting side of the transparent polymeric substrate in a roll-to-roll fashion.

6. The method of any of embodiments 1 to 5, wherein after comparing the first fluorescence emission spectrum and the second fluorescence emission spectrum, further comprising:
curing the photocurable or thermally curable composition sufficient to cure at least 10 weight % of the photocurable or thermally curable component.

7. The method of any of embodiments 1 to 6 that is carried out when the photocurable or thermally curable composition is provided within a delivery reservoir.

8. The method of any of embodiments 1 to 7, wherein the photocurable or thermally curable composition comprises metal particles that have a particle size of at least 0.01 µm and up to and including 25 µm.

9. The method of any of embodiments 1 to 8, wherein the photocurable or thermally curable composition comprises metal particles that are carbon-coated silver particles or carbon-coated copper particles.

10. The method of any of embodiments 1 to 9, wherein the pyrene is present in the photocurable or thermally curable composition in an amount of at least 0.0001 weight % and up to and including 10 weight % based on the total solids in the photocurable composition.

11. The method of any of embodiments 1 to 10, wherein the photocurable or thermally curable composition further comprises one or more free radically polymerizable compounds as a photocurable component, and one or more free radical photoinitiators.

12. The method of any of embodiments 1 to 11, wherein comparing the first fluorescence emission spectrum and the second fluorescence emission spectrum is carried out by comparing first and second predetermined emission peaks in the first fluorescence emission spectrum and the second fluorescence emission spectrum.

The following Examples are provided to illustrate the practice of this invention and are not meant to be limiting in any manner.

Invention Example 1

This examples illustrates the use of pyrene as a probe to monitor the photocuring of a photocurable composition in the form of a thin film.

Pyrene (1 weight %) was added to a solution of the photocurable resin SU-8 3010 (from MicroChem) containing crosslinkable epoxy groups, dissolved in cyclopentanone. The resulting photocurable composition was spin coated onto a glass plate (transparent substrate) and dried at 90° C. for 30 minutes to form a uniform dried photocurable layer. A first fluorescence emission spectrum emitted by pyrene was then recorded. The dried photocurable layer was exposed to light at 365 nm using a medium pressure mercury lamp for 1 minute and was then heated for 1 minute at 100° C.

A second fluorescence emission spectrum emitted by pyrene was then recorded and the dried photocured layer was heated at 130° C. for 1 minute and a third fluorescence spectrum of pyrene was recorded. The photocured layer was further heated at 150° C. for another 1 minute and a fourth fluorescence spectrum emitted by pyrene was recorded. Heating of the photocured layer was continued for additional 2 minutes at 170° C. and a fifth fluorescence emission spectrum emitted by pyrene was then recorded.

FIG. 1 shows the five fluorescence emission spectra emitted by pyrene in the coating.

The photocured coating had reached near completion of curing when the ratio of emission peaks at 375 nm and 395 nm reached some an essentially constant value. The data in FIG. 1 show the fluorescence emission spectra emitted by pyrene in the composition as a function of cure. TABLE I below shows that as the ratio of emission intensity of peak 1 (at 375 nm) to emission intensity of peak 2 (395 nm) reached 0.7 photocuring was about 75% complete (see Column 5 in TABLE I). The progress (extent) of photocuring was also monitored by infrared spectroscopy, using ATR-IR (attenuated total reflectance-infrared spectroscopy) spectra wherein samples were recorded and the extent of epoxy crosslinking (in the photocurable resin) was calculated by quantitative integration of the band at 912 cm$^{-1}$ (due to epoxy ring) in the IR spectra. As photocuring continued, the area under the band at the 912 cm$^{-1}$ peak decreased and the percentage of photocuring was calculated using a ratio of the area of the 912 cm$^{-1}$ peak to the total area under reference 827 cm$^{-1}$ peak due to aromatic rings (this area does not change during curing).

TABLE I

| | $I^{375}$ Intensity (counts/sec) of fluorescence peak @ 375 nm | $I^{395}$ Intensity (counts/sec) of fluorescence peak @ 395 nm | $I^{375}/I^{395}$ | % Cure (by IR spectroscopy) |
|---|---|---|---|---|
| Start (before exposure) | 4974858 | 4272358 | 1.16 | 0 |
| UV Exposed and heated at 100° C. for 1 minute | 3205760 | 2992954 | 1.07 | 45 |
| Further heating at 130° C. for 1 minute | 1787863 | 2310728 | 0.77 | 70 |
| Further heating at 150° C. for 1 minute | 1524660 | 2062238 | 0.73 | 75 |
| Further heating at 170° C. for 1 minute | 1037819 | 1431281 | 0.72 | 80 |
| Further heating at 170° C. for 5 minutes | 811411 | 1135292 | 0.71 | |

Invention Example 2

This example illustrates use of pyrene as a probe to monitor differences in extent of photocuring between top surface and bottom surface of a photocurable composition comprising an epoxy and metal nanoparticles.

A photopolymerizable composition according to the present invention was prepared by mixing 14.3 weight % of epoxy acrylates CN 153 (3.18 g, Sartomer), 10 weight % of poly(ethylene glycol) diacrylate (2.19 g, M$_n$ of 250, Aldrich), 2.1 weight % of poly(ethylene glycol) diacrylate (0.47 g, M$_n$ of 575, Aldrich), 11 weight % of pentaerythritol tetraacrylate (2.40 g, Sartomer), 1 weight % of a triaryl sulfonium salt hexafluorophosphate mixed in 50% propylene carbonate (0.177 g, Aldrich), 1 weight % a triaryl sulfonium salt hexafluoroantimonate mixed in 50% propylene carbonate (0.177 g from Aldrich), 2.4 weight % of free radical photoinitiator hydroxycyclohexyl phenyl ketone (0.53 g, Aldrich), 1.2 weight % of free radical photoinitiator methyl-4'-(methylthio)-2-morpholinopropiophenone (0.27 g, Aldrich), 20 weight % of silver nanoparticles (431 g, from NovaCentrix, advertized as having 20 nm average particle size), 1.1 weight % of carbon nanoparticles (0.243 g), 1 weight % of pyrene (Aldrich), and 35.8 weight % of 1-methoxy isopropanol solvent (7.74 g).

The resulting polymerizable composition was printed using a flexographic printing plate onto a poly(ethylene terephthalate) film substrate to form a dry uniform film having about 0.4 μm thickness. The resulting article was then irradiated using a 200 W medium pressure mercury lamp providing irradiation wavelength of between 190-1500 nm.

Figure 2:
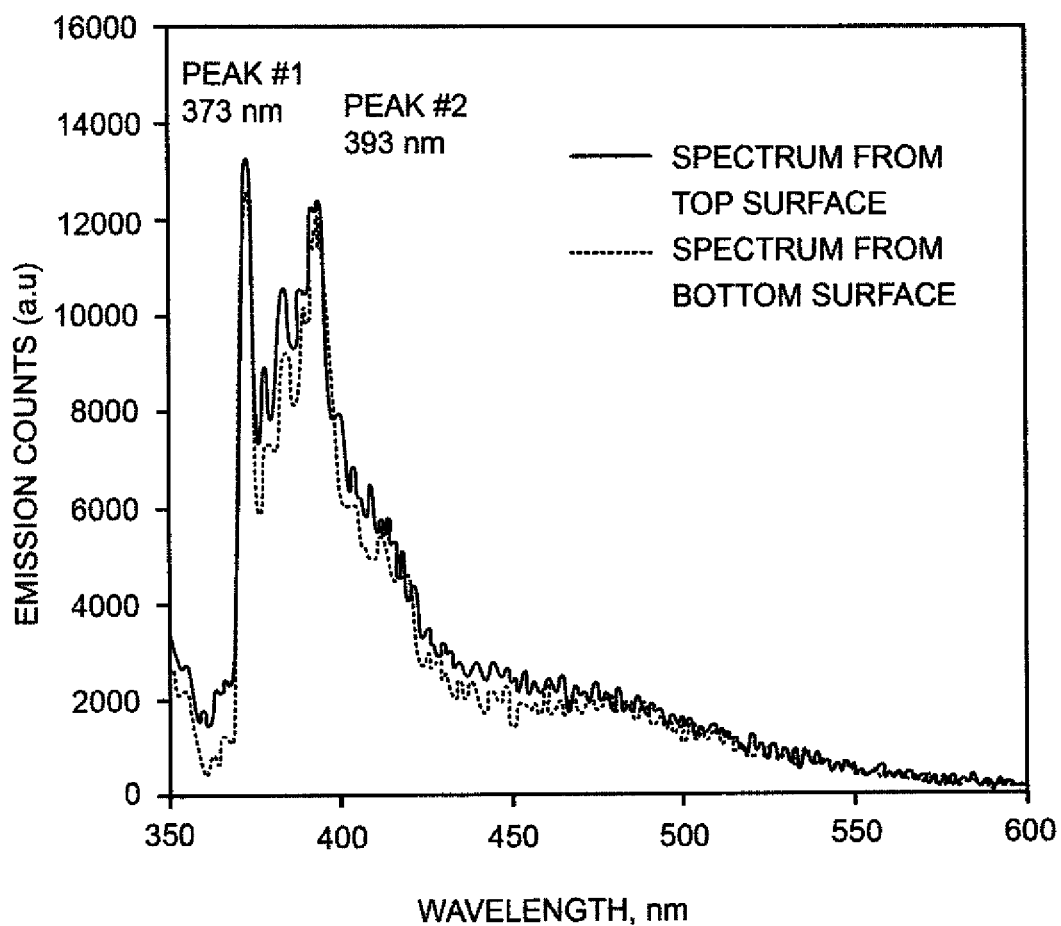
FIG. 2 is a fluorometric spectrum showing results of fluorometric emissions described in Invention Example 2 below.

A first fluorescence emission spectrum emitted by pyrene from the top surface was then recorded. The article was then turned over and a second fluorescence emission spectrum emitted by pyrene from bottom surface was recorded. The ratios of fluorescence peak #1 at 373 nm to fluorescence peak #2 at 393 nm from top surface and bottom surface were compared. See FIG. 2 for fluorescence spectra from top and bottom surfaces and Table II for a comparison of the fluorescence peak ratios from top and bottom surfaces. If the extent of cure was uniform the ratios should have been very similar. However, it was found that ratios were different, clearly indicating differing degrees of curing at the top and bottom surfaces.

TABLE II

| Emission from Top Surface | Emission from Bottom Surface |
|---|---|
| Peak #1 @ 373 nm | Peak #1 @ 373 nm |
| Peak #1 @ 393 nm | Peak #1 @ 393 nm |
| 1.099 | 1.027 |

The invention has been described in detail with particular reference to certain preferred embodiments thereof, but it will be understood that variations and modifications can be effected within the spirit and scope of the invention.

The invention claimed is:

1. A method for determining the extent of curing in a layer of a photocurable or thermally curable composition, the method comprising:
   providing a dried layer of a photocurable or thermally curable composition over a supporting side of a transparent polymeric substrate, the dried layer having an outermost surface and an innermost surface, and the photocurable or thermally curable composition comprising a photocurable or thermally curable component and pyrene,
   exposing the photocurable or thermally curable composition to form an at least partially photocured or thermally cured composition in an at least partially photocured or thermally cured dried layer having an innermost surface and an outermost surface,
   determining a first fluorescence emission spectrum emitted by the pyrene at the innermost surface of the at least partially photocured or thermally cured dried layer,
   determining a second fluorescence emission spectrum emitted by the pyrene at the outermost surface of the at least partially photocured or thermally cured dried layer,
   comparing the first fluorescence emission spectrum and the second fluorescence emission spectrum to determine any difference in curing between the outermost surface and the innermost surface of the at least partially photocured or thermally cured dried layer.

2. The method of claim 1, comprising providing the photocurable or thermally curable composition on a supporting side of a transparent polymeric substrate in a patternwise manner, the transparent polymeric substrate also comprising an opposing second supporting side.

3. The method of claim 2 comprising providing the photocurable or thermally curable composition as multiple patterns on the supporting side of the transparent polymeric substrate that is a transparent polymeric web.

4. The method of claim 2 comprising providing the photocurable or thermally curable composition as multiple patterns on the supporting side of the transparent polymeric substrate in a roll-to-roll fashion.

5. The method of claim 1, wherein the photocurable component is a photopolymerizable epoxy material.

6. The method of claim 1, wherein the exposing is sufficient to photocure at least 10 weight % of the photocurable component.

7. The method of claim 1, wherein the photocurable or thermally curable composition further comprises metal particles that have a particle size of at least 0.01 µm and up to and including 25 µm.

8. The method of claim 7, wherein the photocurable or thermally curable composition further comprises metal particles that are carbon-coated silver particles or carbon-coated copper particles.

9. The method of claim 5, wherein the photocurable composition further comprises a photoacid generator that is an iodonium or sulfonium salt.

10. The method of claim 1, wherein the pyrene is present in the photocurable or thermally curable composition in an amount of at least 0.0001 weight % and up to and including 10 weight % based on the total solids in the photocurable or thermally curable composition.

11. The method of claim 1, wherein the photocurable composition comprises one or more free radically polymerizable compounds as the photocurable component, and further comprises one or more free radical photoinitiators.

12. The method of claim 1, wherein comparing the first fluorescence emission spectrum and the second fluorescence emission spectrum is carried out by comparing first and second predetermined emission peaks in the first fluorescence emission spectrum and the second fluorescence emission spectrum.

13. The method of claim 1, wherein the dried layer has an average dry thickness of at least 0.1 µm and up to and including 10,000 µm.

* * * * *